United States Patent
Tsang et al.

(10) Patent No.: US 7,476,673 B2
(45) Date of Patent: Jan. 13, 2009

(54) DISUBSTITUTED CHALCONE OXIMES AS SELECTIVE AGONISTS OF RAR$_\gamma$ RETINOID RECEPTORS

(75) Inventors: Kwok Yin Tsang, Irvine, CA (US); Santosh Sinha, Ladera Ranch, CA (US); Xiaoxia Liu, Lake Forest, CA (US); Smita Bhat, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 532 days.

(21) Appl. No.: 11/015,994

(22) Filed: Dec. 17, 2004

(65) Prior Publication Data

US 2005/0148590 A1    Jul. 7, 2005

Related U.S. Application Data

(60) Provisional application No. 60/533,733, filed on Dec. 30, 2003.

(51) Int. Cl.
| | |
|---|---|
| *A61K 31/50* | (2006.01) |
| *A61K 31/4965* | (2006.01) |
| *A61K 31/497* | (2006.01) |
| *A61K 31/47* | (2006.01) |
| *A61K 31/38* | (2006.01) |
| *A61K 31/15* | (2006.01) |
| *A01N 43/54* | (2006.01) |
| *A01N 43/42* | (2006.01) |
| *A01N 43/18* | (2006.01) |
| *A01N 43/16* | (2006.01) |
| *A01N 33/24* | (2006.01) |
| *C07D 239/42* | (2006.01) |
| *C07D 401/04* | (2006.01) |
| *C07D 401/00* | (2006.01) |
| *C07D 403/00* | (2006.01) |
| *C07D 405/00* | (2006.01) |
| *C07D 411/00* | (2006.01) |
| *C07D 413/00* | (2006.01) |
| *C07D 417/00* | (2006.01) |
| *C07D 239/02* | (2006.01) |
| *C07D 241/36* | (2006.01) |
| *C07D 215/12* | (2006.01) |
| *C07D 335/04* | (2006.01) |
| *C07D 335/06* | (2006.01) |
| *C07D 409/00* | (2006.01) |
| *C07D 495/00* | (2006.01) |
| *C07D 319/14* | (2006.01) |
| *C07D 291/00* | (2006.01) |
| *C07C 249/00* | (2006.01) |
| *C07C 251/00* | (2006.01) |
| *C07C 259/00* | (2006.01) |

(52) U.S. Cl. .............. 514/249; 514/252.01; 514/252.02; 514/252.04; 514/252.06; 514/252.11; 514/256; 514/312; 514/432; 514/456; 514/457; 514/640; 544/238; 544/295; 544/333; 544/335; 544/353; 546/176; 549/23; 549/366; 564/265

(58) Field of Classification Search ................. 514/249, 514/252.01, 252.02, 252.04, 252.06, 252.11, 514/256, 312, 432, 456, 457, 640; 544/238, 544/295, 333, 335, 353; 546/176; 549/23, 549/366; 564/265
See application file for complete search history.

(56) References Cited

U.S. PATENT DOCUMENTS

| | | |
|---|---|---|
| 5,455,265 A | 10/1995 | Chandraratna |
| 5,599,967 A | 2/1997 | Vuligonda et al. |
| 5,605,915 A | 2/1997 | Vuligonda et al. |
| 5,723,666 A | 3/1998 | Vuligonda et al. |
| 5,739,338 A | 4/1998 | Beard et al. |
| 5,760,276 A | 6/1998 | Beard et al. |
| 6,107,458 A | 8/2000 | Ohki et al. |
| 6,225,494 B1 | 5/2001 | Song et al. |
| 6,303,785 B1 | 10/2001 | Vasudevan et al. |
| 6,403,810 B2 | 6/2002 | Klaus et al. |
| 6,455,701 B1 | 9/2002 | Song et al. |
| 6,469,028 B1 | 10/2002 | Klein et al. |
| 6,492,414 B1 | 12/2002 | Chandraratna et al. |

FOREIGN PATENT DOCUMENTS

| | | |
|---|---|---|
| WO | WO 93/11755 | 6/1993 |
| WO | WO 02/28810 A2 | 4/2002 |
| WO | WO 02/077169 A2 | 10/2002 |

OTHER PUBLICATIONS

R. Marks "The role of tazarotene in the treatment of psoriasis" British Journal of Dermatology, vol. 140 (Suppl. 54), pp. 24-28 (1999).*

(Continued)

*Primary Examiner*—Zachary C Tucker
(74) *Attorney, Agent, or Firm*—Hamilton, Brook, Smith & Reynolds, P.C.

(57) ABSTRACT

Compounds of the formula

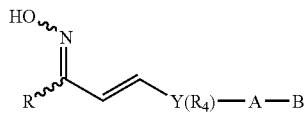

where the variables are as defined in the specification, are useful for preventing or treating emphysema and related pulmonary conditions of mammals and other diseases and conditions which are responsive to RAR$_\gamma$ agonist retinoids, such as skin related diseases, including but not limited to acne and psoriasis.

38 Claims, No Drawings

OTHER PUBLICATIONS

Bagade and Ghiya, "Reaction of Oximes of 2-Hydroxyacetophenone, Chalcone, Flavanone, and Flavone" Asian Journal of Chemistry, vol. 3(2), pp. 158-163 (1991), as abstracted by CAS online.*

Bagade and Ghiya, "Reaction in Oximes of 2-Hydroxyacetophenone, Chalcone, Flavanone and Flavone" Asian Journal of Chemistry, vol. 3(2), pp. 158-163 (1991).*

Mangelsdorf et al. (1994) The Retinoid Receptors In: The Retinoids, edited by Sporn et al. p. 319-349. Raven Press, Ltd., New York.

Dawson and William H. Okamura, Chemistry and Biology of Synthetic Retinoids, Published by CRC Press Inc., 1990, pp. 324-356.

Feigner P. L. and Holm M. (1989) Focus, 112.

Heyman et al. Cell 68, 397-406, (1992).

Allegretto et al. J. Bio Chem. 268, 26625-26633.

Cheng et al. Biochemical Pharmacology vol. 22 pp. 3099-3108.

Raleigh et al., Proc. Amer. Assoc. Cancer Research Annual Meeting, 1999, 40, 397.

* cited by examiner

DISUBSTITUTED CHALCONE OXIMES AS SELECTIVE AGONISTS OF RAR$_\gamma$ RETINOID RECEPTORS The present application claims the priority of provisional application Ser. No. 60/533,733 filed on Dec. 30, 2003.

BACKGROUND OF THE INVENTION

1. Field of the Invention

The present invention is directed to compounds having specific or selective activity as agonists of RAR$_\gamma$ retinoid receptors. More specifically, the present invention is directed to disubstituted chalcone oximes that have specific or selective activity as agonists of RAR$_\gamma$ retinoid receptors.

2. Background Art

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated RAR$_\alpha$, RAR$_\beta$ and RAR$_\gamma$, in RXR the subtypes are: RXR$_\alpha$, RXR$_\beta$ and RXR$_\gamma$. It has also been established in the art that the distribution of the two main retinoid receptor types, and of the several subtypes is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319-349. Raven Press, Ltd., New York. For another general overview see Dawson and William H. Okamura, Chemistry and Biology of Synthetic Retinoids, published by CRC Press Inc., 1990, pages 324-356.

Relatively recently it has been discovered that compounds which are selective or specific agonists (ligands) of RAR$_\gamma$ retinoid receptors are capable of preventing or treating alveolar destruction in the lungs of mammals, or are capable of promoting the formation of alveoli in mammalian lungs which are deficient in adequate numbers of functional alveoli. Thus, such specific or selective agonists of RAR$_\gamma$ retinoid receptors are useful for the prevention or treatment of emphysema and related pulmonary insufficiency diseases or conditions. See U.S. Pat. No. 6,492,414 assigned to the same assignee as the present application:

U.S. Pat. No. 6,403,810 describes vinyl compounds substituted with a thiophene group and with an indan, tetrahydrobenzofuran, tetrahydrobenzothiophene or tetrahydrobenzopyrrole group useful for treating emphysema and associated pulmonary diseases. PCT Publication WO 02/28810 A2 also discloses compounds useful for treating emphysema and associated pulmonary diseases and the general formulas provided in this disclosure include chalcone oxime compounds.

"Chalcone moiety" or "chalcone linker" and "chalcone oxime linker" are terms for describing in this application moieties that have the structure shown below

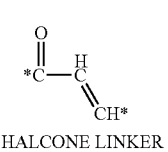
CHALCONE LINKER

CHALCONE OXIME LINKER and which in the present invention covalently link two aromatic or heteroaromatic moieties. In the formula the stars indicate the carbons to which the aromatic rings are attached, respectively.

The following references disclose retinoid compounds which are disubstituted "chalcone" compounds: U.S. Pat. Nos. 6,455,701; 6,469,028; 6,225,494; 5,723,666; 5,739,338 and 5,760,276.

U.S. Pat. Nos. 5,723,666; 5,599,967; and 5,605,915 disclose retinoid compounds which include an oxime moiety.

SUMMARY OF THE INVENTION

The present invention relates to compounds of Formula 1

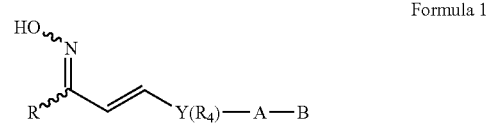
Formula 1 wherein R is selected from the groups consisting of the radicals defined by formulas (a) through (g)

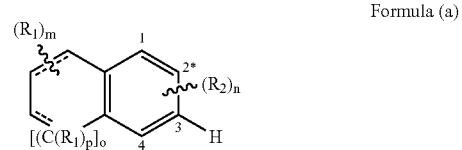
Formula (a)

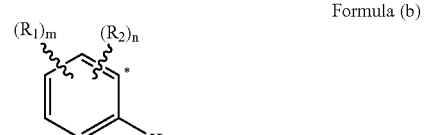
Formula (b)

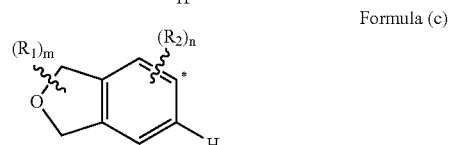
Formula (c)

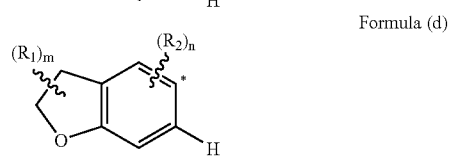
Formula (d)

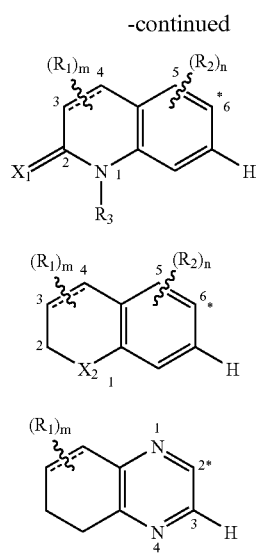

where the dashed line in a ring represents a bond, or absence of a bond with the proviso that only one of the two dashed lines in the ring can represent a bond;
- a * denotes a ring carbon to which the chalcone oxime group is attached;
- $X_1$ is O or S attached to the adjacent carbon with a double bond, or $X_1$ represents two $R_1$ groups attached to the adjacent carbon;
- $X_2$ is O or S;
- Y is a phenyl or naphthyl group, or heteroaryl selected from a group consisting of pyridyl, thienyl, furyl, pyridazinyl, pyrimidinyl; pyrazinyl, thiazolyl, oxazolyl, imidazolyl and pyrrazolyl, said phenyl and heteroaryl groups being optionally substituted with one or two $R_4$ groups;
- m is an integer having the values 0 to 6;
- n is an integer having the values 0 to 2;
- o is an integer having the values 0 or 1;
- p is an integer having the values 1 or 2;
- $R_1$ is independently alkyl of 1 to 6 carbons, $COOR_3$, F, Cl, Br or I;
- $R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
- $R_3$ is H or alkyl of 1 to 10 carbons;
- $R_4$ is independently halogen, alkyl of 1 to 10 carbons, fluoro substituted alkyl of 1 to 6 carbons, alkoxy of 1 to 10 carbons, or alkylthio of 1 to 10 carbons;
- A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
- B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 1.0 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

The present invention also relates to pharmaceutical compositions incorporating the compounds of Formula 1 and to methods of treatment of emphysema and related pulmonary conditions of mammals with pharmaceutical compositions containing one or more compounds of Formula 1.

The present invention also relates to the methods of using the compounds of the invention to treat diseases and conditions which are responsive to treatment by RARE agonist retinoids, such as skin related diseases including but not being limited to acne and psoriasis

DETAILED DESCRIPTION OF THE INVENTION

GENERAL EMBODIMENTS AND SYNTHETIC METHODOLOGY

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include at least one olephinic double bond about which trans and cis (E and Z) stereoisomerism can exist. The compounds of the present invention have the specific orientations of substituents relative to the double bond or double bonds, as is indicated in the name of the respective compound, and/or by specific showing in the structural formula of the orientation of the substituents relative to the double bond or double-bonds.

The compounds of the invention also include an oxime function that is attached to the adjacent carbon by a double bond about which syn and anti stereoisomerism exists. The scope of the invention is intended to cover oximes in both syn and anti configuration. However, the specific examples have the specific configuration that is indicated in their respective chemical names and/or is shown by the respective structural formulas.

The compounds of the present invention may also contain one or more chiral centers and therefore may exist in enantiomeric and diastereomeric forms. With regard to the chiral centers in the compounds, the scope of the invention is intended to cover all possible orientations of the substituents, thus including pure enantiomers (optical isomers), diastereomers, mixtures of diastereomers and racemic mixtures of enantiomers.

Generally speaking the compounds of the invention can be obtained by the synthetic route shown in Reaction Scheme 1.

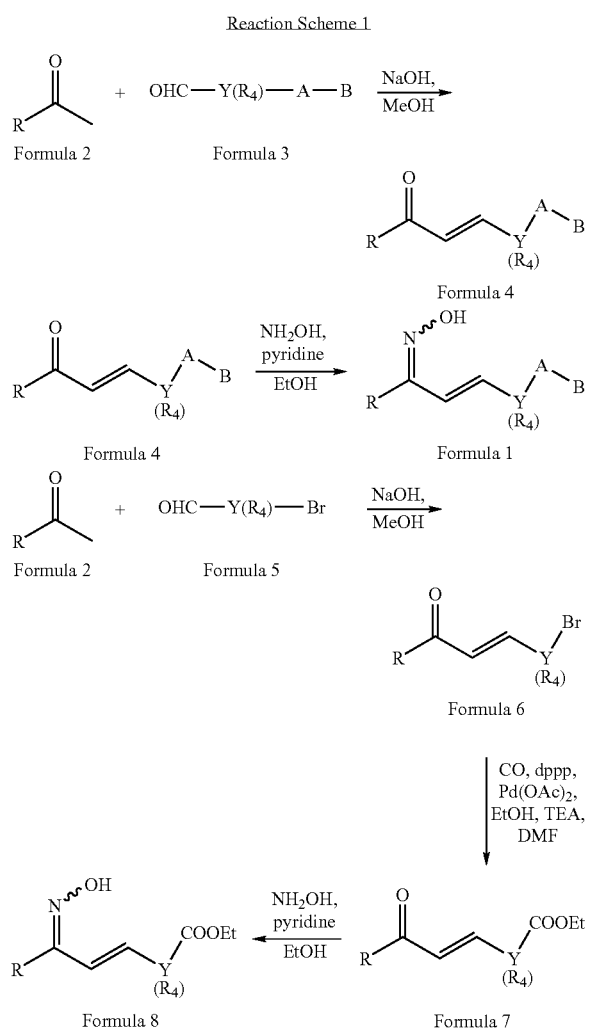

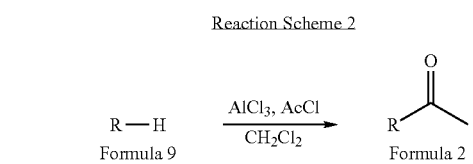

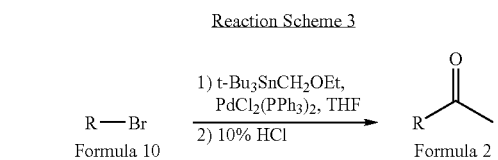

The chalcone compound of Formula 7 is then converted to the oxime of Formula 8 by reaction with hydroxylamine in the presence of pyridine or other base. The compounds of Formula 8 are within the scope of the invention and within the scope of Formula 1.

The methyl ketones of Formula 2 are usually available in accordance with the chemical patent and/or scientific literature, or can be obtained by such modifications of known synthetic methods which are readily within the skill of the practicing organic chemist. Reaction Schemes 2 and 3 disclose general synthetic routes that provide the methyl ketone of Formula 2.

In accordance with Reaction Scheme 2 a compound of Formula 9 is subjected to a Friedel Crafts reaction with acetyl chloride in a suitable aprotic solvent, such as methylene chloride, to provide the methyl ketone of Formula 2. In accordance with Reaction Scheme 3 a bromo compound of Formula 10 is reacted in a suitable aprotic solvent, such as tetrahydrofuran (THF), under a protective blanket of an inert gas, such as argon, with tributyl(1-ethoxyvinyl)tin in the presence of a palladium catalyst ($PdCl_2(PPh_3)_2$), and thereafter with acid to provide the methyl ketone of Formula 2. The starting materials in these reactions, namely the compounds of Formulas 9 and 10 are available in accordance with the chemical patent and/or scientific literature, or can be obtained by such modifications of known synthetic methods which are readily within the skill of the practicing organic chemist. Numerous examples for the compounds of Formulas 2, 9 and 10 are provided in connection with the specific examples disclosed below together, where applicable, with the presently preferred method for synthesizing these compounds.

The aromatic or heteroaromatic aldehyde reagents of Formulas 3 and 5 in Reaction Scheme 1 where the variables Y, $R_4$, A and B are defined as in connection with Formula 1 are also available in accordance with the chemical patent and/or scientific literature, or can be obtained by such modifications of known synthetic methods which are readily within the skill of the practicing organic chemist.

The starting compound in Reaction Scheme 1 is a methyl ketone of Formula 2 where the variable R is defined as in connection with Formula 1. The methyl ketone of Formula 2 is reacted with an aldehyde of Formula 3 in the presence of strong base, such as sodium hydroxide, in a suitable polar solvent, such as methanol. The result of this aldol condensation reaction is a compound of Formula 4 where the R group and the substituted aromatic or heteroaromatic Y group are covalently linked with the chalcone moiety CO=CH=CH. The compound of Formula 4 is then reacted in a suitable polar solvent, such as ethyl alcohol, with hydroxylamine in the presence of pyridine to provide: the oxime compounds of the invention of Formula 1. Usually oximes of both syn and anti (or cis and trans) configuration are formed in the last reaction, but not necessarily in equal amounts. In most instances the isomeric oximes can be separated from each other by crystallization and/or chromatography.

In a variation of the synthetic route shown in Reaction Scheme 1 the A-B group of Formula 3 is replaced with a bromo group as shown in Formula 5. In this variation, after the aldol condesation reaction the product (Formula 6) is converted to a compound of Formula 7 by reaction with carbon monoxide in the presence of 1,3-bis(diphenylphosphino)propane (dppp) and palladium acetate in dimethylformamide (DMF), triethylamine (TEA) and anhydrous ethanol.

Examples for the aromatic or heteroaromatic aldehyde reagents of Formulas 3 and 5 usable in Reaction Scheme 3 are methyl-4-formylbenzoate, methyl 4-formyl-2-fluoro-benzoate, 4-bromo-2-fluoro-benzaladehyde, 4-bromobenzaldehyde, methyl-3-formylbenzoate, methyl 3-formyl-2-fluoro-benzoate, 3-bromo-2-fluoro-benzaladehyde, 3-bromobenzaldehyde, methyl-5-formyl-naphthoate, methyl-6-formyl-naphthoate, methyl-5-formyl-thiophene-2-carboxylate, methyl-5-formyl-thiophene-3-carboxylate, methyl-5-formyl-furan-2-carboxylate, methyl-5-formyl-furan-3-carboxylate, methyl-6-formyl-pyridine-2-carboxylate, methyl-6-formyl-pyridine-3-carboxylate, 1-bromo-5-formyl-naphthalene, 1-bromo-4-formyl-naphthalene, 2-bromo-5-formyl-thiophene, 3-bromo-5-formyl-thiophene, 2-bromo-5-formyl-furan, 3-bromo-5-formyl-furan, 3-bromo-6-formyl-pyridine and 2-bromo-6-formyl-pyridine.

Biological Activity, Modes of Administration

The compounds of the invention were tested in certain assays for activity as agonists of RAR and RXR retinoid receptors. Specifically, one such assay is a chimeric receptor transactivation assay which tests for agonist-like activity in the $RAR_\alpha$, $RAR_\beta$ and $RAR_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30-33 and 37-41) published on Jun. 24, 1993, the specification of which is also incorporated herein by reference. A detailed experimental procedure for holoreceptor transactivations has been described by Heyman et al. Cell 68, 397-406, (1992); Allegretto et al. J. Biol. Chem. 268, 26625-26633, and Mangelsdorf et al. The Retinoids: Biology, Chemistry and Medicine, pp 319-349, Raven Press Ltd., New York, which are expressly incorporated herein by reference. The results obtained in this assay are expressed in $EC_{50}$ numbers, as they are also in the chimeric receptor transactivation assay. The results of the ligand binding assay are expressed in $K_i$ numbers. (See Cheng et al. Biochemical Pharmacology Vol. 22 pp 3099-3108, expressly incorporated herein by reference.)

Efficacy in a transactivation assay is expressed as a percentage of the maximum potency attained by the compound compared to a standard which, in this case, is the compound 4-[(1E)-2-(5,6,7,8-tetrahydro-5,5,8,8-tetramethyl-2-naphthalenyl)-1-propenyl]-benzoic acid. (TTNPB) This standard compound is described in PCT Publication WO 2002077169 A2.

Table 1 discloses the activity of certain exemplary compounds of the invention in the above-described chimeric RAR receptor transactivation and binding assays. In the holoreceptor transactivation assay the compounds were relatively inactive in activating $RXR_\alpha$, $RXR_\beta$ and $RXR_\gamma$ receptors.

TABLE 1

| Compound | RAR Binding (nM) | | | RAR EC50 (nM) (% Efficiency) | | |
|---|---|---|---|---|---|---|
| | α | β | γ | α | β | γ |
| 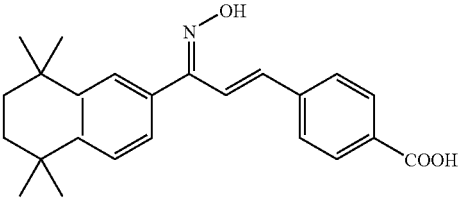 3a | 2.5k | 1.3k | 3 | 441 (81%) | 31 (102%) | 0.09 (103%) |
| 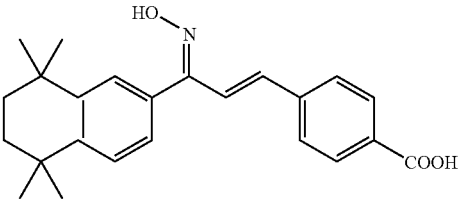 3b | 2.4k | 2k | 14 | 150 (81%) | 34 (112%) | 0.37 (114%) |
| 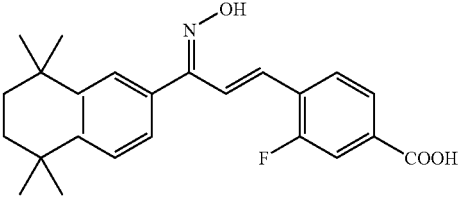 5a | 8k | 5k | 4 | >1k | 53 (84%) | 0.11 (84%) |

TABLE 1-continued
| Compound | RAR Binding (nM) | | | RAR EC50 (nM) (% Efficiency) | | |
|---|---|---|---|---|---|---|
| | α | β | γ | α | β | γ |
| 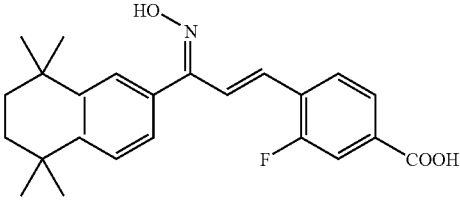 5b | 8k | 8k | 34 | >1k | 118 (85%) | 0.85 (76%) |
| 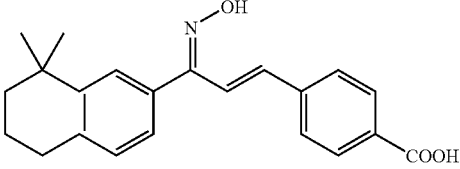 18a | 6k | 1.2k | 5 | 2118 (51%) | 65 (106%) | 0.09 (97%) |
| 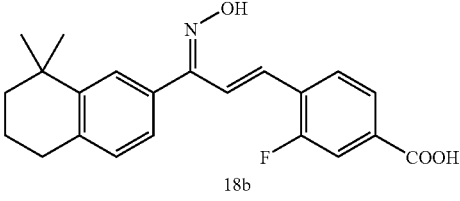 18b | 5.2k | 1.2k | 46 | 118 (39%) | 62 (133%) | 44 (97%) |
| 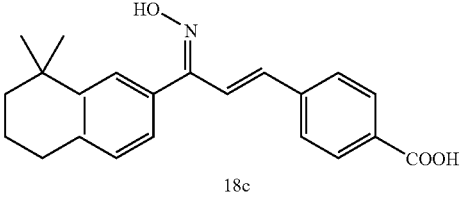 18c | 22k | 4.7k | 16 | >1k | 432 (88%) | 3 (98%) |
| 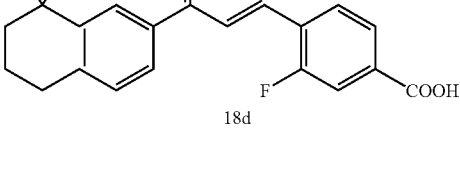 18d | 2.1k | 7k | 132 | 345 (120%) | 4058 (95%) | 14 (123%) |
| 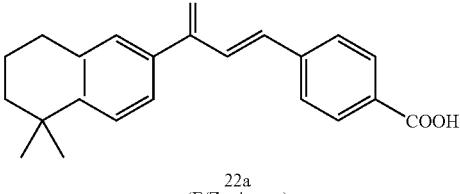 22a (E/Z mixture) | 2k | >10k | 6k | >10k | >10k | >10k |

TABLE 1-continued
| Compound | RAR Binding (nM) | | | RAR EC50 (nM) (% Efficiency) | | |
|---|---|---|---|---|---|---|
| | α | β | γ | α | β | γ |
| 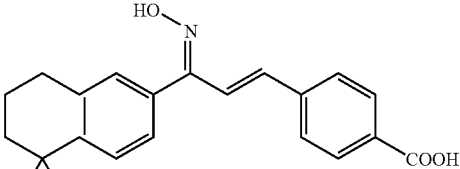  22b | 12k | 31k | 27k | 12k (42%) | 173 (60%) | 204 (65%) |
| 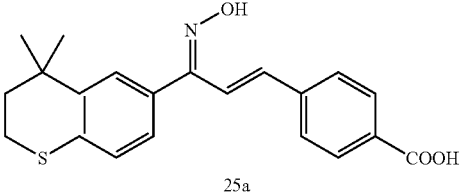  25a | 5k | 1085 | 6 | 242 (117%) | 79 (87%) | 0.75 (88%) |
| 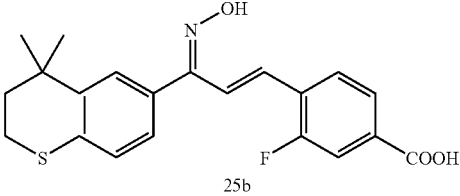  25b | 10k | 8k | 15 | >1k | 173 (55%) | 10 (90%) |
| 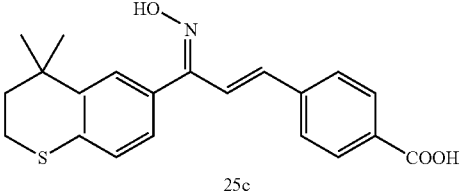  25c | 4.5k | 1228 | 55 | >1k | 103 (102%) | 15 (100%) |
| 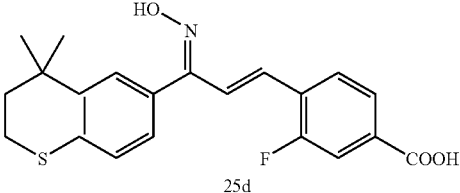  25d | 10k | 10k | 19 | >1k | 503 (45%) | 21 (120%) |
| 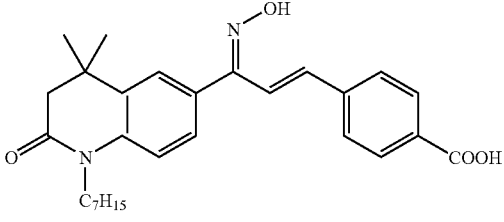  31a | 11k | 29k | 51 | >1k | >k | 10 (11%) |

TABLE 1-continued

| Compound | RAR Binding (nM) | | | RAR EC50 (nM) (% Efficiency) | | |
|---|---|---|---|---|---|---|
| | α | β | γ | α | β | γ |
| 31b (E/Z mixture) | 17k | 9k | 32 | >1k | 473 (23%) | 92 (35%) |
| 34a | >10k | >10k | >10k | >10k | >10k | >10k |
| 34b | 5k | 5k | 10k | 135 (60%) | 93 (97%) | 57 (95%) |
| 39a | 3k | 1.3k | 6 | 7000 (38%) | 54 (95%) | 0.3 (91%) |
| 39b | 7k | 11k | 256 | >1k | 168 (86%) | 2 (92%) |
| 39c | 4k | 3k | 36 | 515 (50%) | 94 (104%) | 4 (95%) |

TABLE 1-continued

| Compound | RAR Binding (nM) | | | RAR EC50 (nM) (% Efficiency) | | |
|---|---|---|---|---|---|---|
| | α | β | γ | α | β | γ |
| 39d | 18k | 11k | 28 | >1k | 445 (92%) | 11 (90%) |
| 44a | 7k | 17k | 6 | 148 (55%) | 83 (104%) | 0.2 (71%) |
| 44b | 6k | 11k | 39 | 134 (55%) | 93 (118%) | 2 (91%) |
| 46a | 14k | 25k | 25 | >1k | 114 (79%) | 1 (72%) |
| 44b | 13k | 27k | 264 | >1k | 249 (82%) | 9 (79%) |
| 48a (E/Z mixture) | 27k | 100k | 240 | 4000 (41%) | 105 (88%) | 10 (123%) |

TABLE 1-continued

| Compound | RAR Binding (nM) | | | RAR EC50 (nM) (% Efficiency) | | |
|---|---|---|---|---|---|---|
| | α | β | γ | α | β | γ |
| 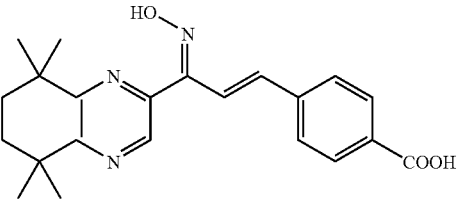 48b | 25k | 100k | 461 | 128 (54%) | 77 (110%) | 143 (151%) |
| 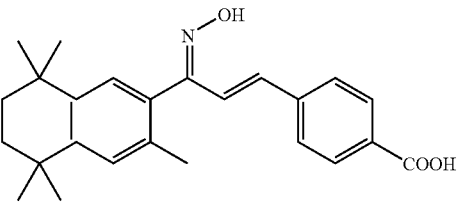 9a | 8k | 17k | 583 | >1k | 3440 (41%) | 23 (48%) |
| 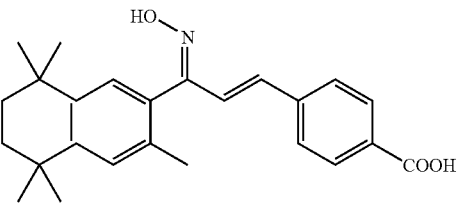 9b | 8k | 28k | 1847 | >1k | 157 (14%) | 35 (67%) |
| 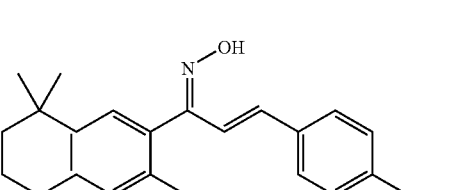 13a | 2k | 2.5k | 648 | 80k (29%) | 1270 (65%) | 19 (98%) |
| 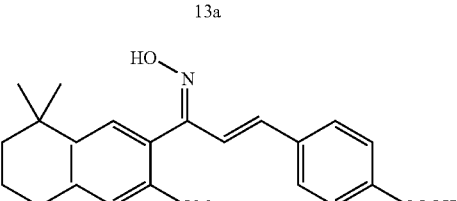 13b | 10k | 10k | 1495 | >1k | 5917 (44%) | 84 (107%) |

As it can be seen the compounds of the invention are specific or selective agonists of the RAR$_\gamma$ retinoid receptors, and as such they are capable of preventing or treating alveolar destruction in the lungs of mammals, or are capable of promoting the formation of alveoli in mammalian lungs which are deficient in adequate numbers of functional alveoli. Thus, the compounds of the invention are useful for the prevention or treatment of emphysema and related pulmonary insufficiency diseases or conditions of mammals, including human beings. The compounds are also useful for treating those diseases or conditions which are responsive to RAR$_\gamma$ agonist retinoids, for example skin related diseases including but not being limited to acne and psoriasis. The data for Compounds 9a, 9b, 13a, and 13b are provided in Table 1 for comparison only. These 4 compounds have a substituent in the 3 position of the tetrahydronaphthalene moiety and are not in the scope of the invention because they are less selective to the RARγ receptors than the compounds of the invention.

Modes of Administration, Dosing

To treat mammals, including humans, in need of such treatment to prevent or treat alveolar destruction in the lungs of the mammal, or to promote the formation of alveoli in the lungs of the mammal, or to prevent or treat emphysema or any related pulmonary condition a pharmaceutical composition containing one or more compounds of the invention is administered to the mammal in daily doses in the range of 1 to 100 mg per kg body weight of the mammal. Preferably the daily dose is between 5 to 20 mg per kg body weight of the mammal.

Generally speaking the compounds of the invention, being agonist of $RAR_\gamma$ retinoid receptors are also useful for preventing or treating diseases and conditions that are responsive to compounds that promote the expression of or bind to $RAR_\gamma$ retinoid receptors. For example the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema and atopic dermatitis Darriers disease, lichen planus, prevention and reversal of glucocorticoid damage (steroid atrophy), as a topical antimicrobial, as skin pigmentation agents and to treat and reverse the effects of age and photo damage to the skin. To treat emphysema or related respiratory conditions the compounds of this invention are preferably administered, orally or directly to the lung by inhalation through an inhaler (See, e.g. Raleigh et al., *Proc. Amer. Assoc. Cancer Research Annual Meeting*, 1999, 40, 397, which is herein incorporated by reference).

For the prevention or treatment of these diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by $RAR_\gamma$ agonist compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

SPECIFIC EMBODIMENTS OF THE COMPOUNDS OF THE INVENTION

Referring now to Formula 1, in the preferred compounds of the invention the variable R represents a substituted 5,6,7,8-tetrahydronapthalen-2-yl radical, a substituted thiochroman-6-yl radical, a substituted 1,2,3,4-tetrahydroquinolin-6-yl radical, a substituted chroman-6-yl radical, a substituted 7,8-dihydronapthalen-2-yl radical, a substituted-indan-6-yl radical, or a substituted 5,6,7,8-tetrahydroquinoxalin-2-yl radical.

In the preferred compounds of the invention $R_1$ independently represents alkyl of 1 to 6 carbons, more preferably alkyl of 1 to 3 carbons, and even more preferably methyl, and the variable m is preferably an integer having the value of 2 to 4.

In the presently preferred compounds of the invention the aromatic portion of the moiety designated R is either unsubstituted with and $R_2$ group (n is zero) or substituted with one or two $R_2$ groups which are preferably alkyl of 1 to 6 carbons, more preferably alkyl of 1 to 3 carbons.

The aromatic or heteroaromatic radical represented by Y is preferably phenyl, pyridyl, thienyl or furyl. Even more preferably Y is phenyl, and more preferably the phenyl group is substituted by the chalcone oxime linker and the A-B group in the 1,4 (para) position. When Y is pyridyl, it is preferably substituted by the chalcone oxime linker and the A-B group in the 2,5 position. The thienyl or furyl groups are preferably substituted by the chalcone oxime linker and the A-B group in the 2,4 or 2,5 positions.

In the preferred compounds of the invention either there is no $R_4$ substituent or $R_4$ represents halogen, and even more preferably a fluoro group. The fluoro group is preferably attached in the 1,2 (ortho) position relative to the chalcone oxime linker.

The A-B group preferably represents $(CH_2)_q$—COOH, $(CH_2)_q$—COOR$_8$, or $(CH_2)_q$—CONR$_9$R$_{10}$. More preferably q is zero (0) and B is COOH, the cation of a pharmaceutically acceptable salt, or $R_8$ is alkyl of 1 to 3 carbons, or methoxymethyl. In the most preferred compounds of the invention $R_8$ is H or the cation of a pharmaceutically acceptable salt.

The structures of the presently most preferred compounds of the invention are shown in Table 1, and the experimental procedures for their syntheses are described below.

Synthesis of Tetrahydronaphthalene Exemplary Compounds of the Invention
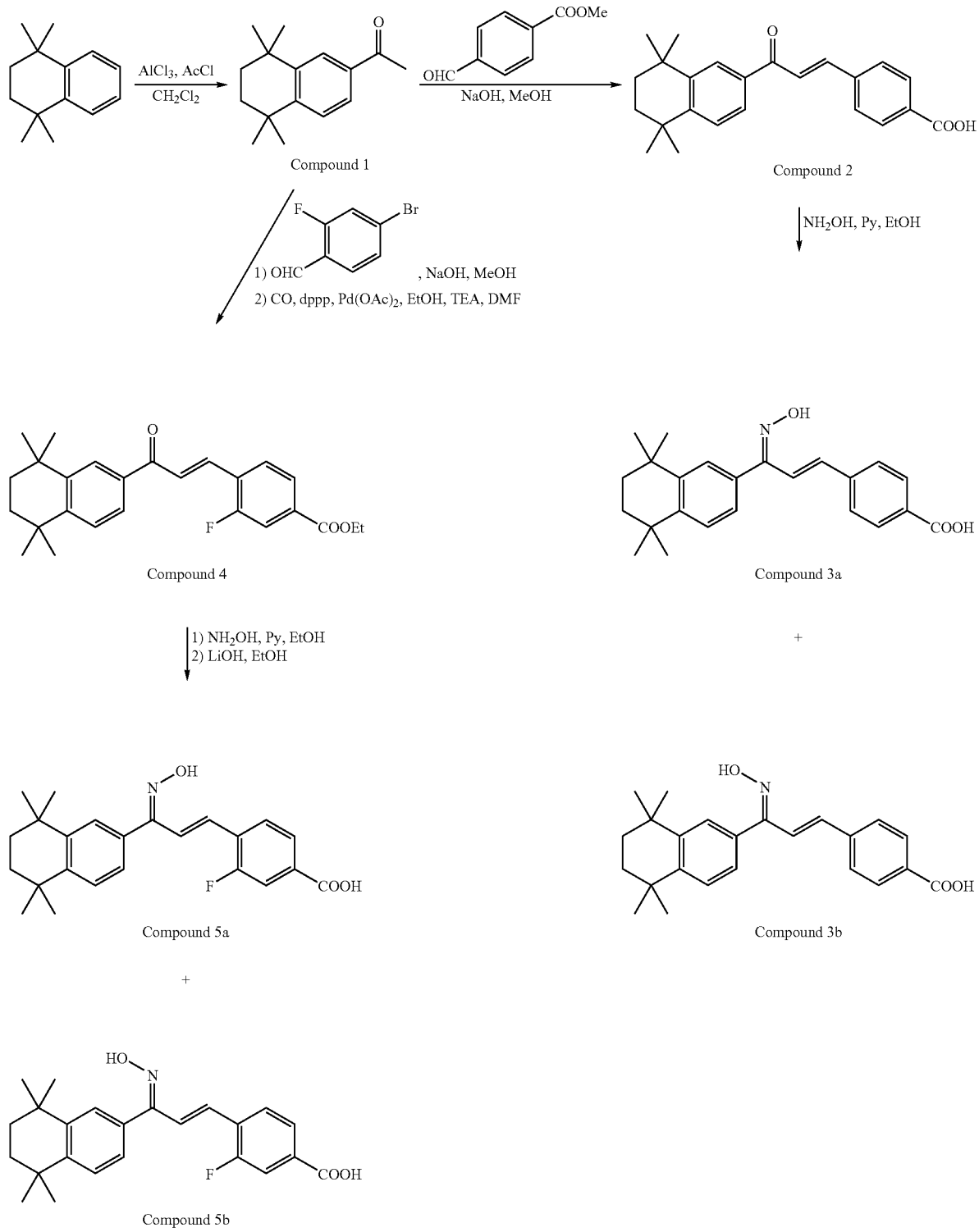

General Procedure A 1-(5,5,8,8-Tetramethyl-5,6,7,8-tetrahydro-naphthalen-2-yl)-ethanone (Compound 1)

Acetyl chloride (2.56 g, 32.6 mmol) was slowly added to a solution of aluminum chloride (4.34 g, 32.6 mmol) in 25 mL of dichloromethane at 0° C. After stirring at 0° C. for 5 min, 1,1,4,4-tetramethyl-1,2,3,4-tefrahydro-naphthalene (available from Ryan Scientific, Inc.) (5.00 g, 21.7 mmol) in 5 mL of dichloromethane was added dropwise to the mixture. The resulting solution was stirred at room temperature for 3 h and poured to 100 mL of ice-water mixture. The organic layer was separated, washed with brine (2×20 mL), dried ($MgSO_4$) and concentrated at reduced pressure to give a light yellow residue. Purification by flash chromatography (90:10 hexane/ethyl acetate) afforded ketone 1 (5.78 g, 98% yield) as a white solid:

$^1$H NMR ($CDCl_3$, 300 MHz) δ 7.93 (d, J=2.1 Hz, 1H), 7.69 (dd, J=2.1, 8.4 Hz, 1H), 7.39 (d, J=8.4 Hz, 1H), 2.57 (s, 3H), 1.70 (s, 4H), 1.31 (s, 6H), 1.29 (s, 6H).

General Procedure B 4-[3-Oxo-3-(5,5,8,8-tetramethyl-5,6,7,8-tetrahydro-naphthalen-2-yl)-propenyl]-benzoic acid (Compound 2)

Methyl 4-formylbenzoate (1.28 g, 7.83 mmol) was added to a solution of 1-(5,5,8,8-tetramethyl-5,6,7,8-tetrahydro-naphthalen-2-yl)-ethanone (Compound 1, 1.80 g, 7.83 mmol) in 10 mL of 1 N NaOH and 20 mL of methanol. After stirring at room temperature for 18 h, the reaction mixture was acidified with 1N HCl and extracted with ethyl acetate (3×10 mL). The combined organic layer was washed with brine (1×10 mL), dried ($MgSO_4$) and concentrated at reduced pressure. Recrystallization (acetonitrile) gave the title compound (1.70 g, 60% yield) as a white solid:

$^1$H NMR ($CDCl_3$, 300 MHz) δ 8.15 (d, J=8.4 Hz, 2H), 8.0 (d, J=1.8 Hz, 1H), 7.81 (d, J=15.6 Hz, 1H), 7.76-7.71 (m, 3H), 7.59 (d, J=15.6 Hz, 1H), 7.44 (d, J=8.4 Hz, 1H), 1.73 (s, 4H), 1.35 (s, 6H), 1.32 (s, 6H).

General Procedure C E-4-[3-Hydroxyimino-3-(5,5,8,8-tetramethyl-5,6,7,8-tetrahydro-naphthalen-2-yl)-propenyl]-benzoic acid (Compound 3a) and Z4-[3-hydroxyimino-3-(5,5,8,8-tetramethyl-5,6,7,8-tetrahydro-naphthalen-2-yl)-propenyl]-benzoic acid (Compound 3b)

To a solution of 4-[3-oxo-3-(5,5,8,8-tetramethyl-5,6,7,8-tetrahydro-naphthalen-2-yl)-propenyl]-benzoic acid (Compound 2, 1.70 g, 4.70 mmol) in 10 mL of EtOH was added hydroxylamine hydrochloride (653 mg, 9.40 mmol) and pyridine (1.86 g, 23.5 mmol). The reaction mixture was then heated at reflux for 6 h. After cooling to room temperature, the solvent was removed in vacuo and the residue was taken up in water. The aqueous layer was adjusted to pH=4-5 with 1 N HCl and extracted with ethyl acetate (3×10 mL). The organic layers were combined and washed with water (2×10 mL) and brine (1×10 mL), dried ($MgSO_4$) and concentrated at reduced pressure. Purification by recrystallization (acetonitrile) followed by flash chromatography (50:50 hexane/ethyl acetate) yielded the title compounds 3a (1.20 g, 68% yield) and 3b (300 mg, 17% yield) as white solids:

$^1$H NMR for Compound 3a ($CD_3OD$, 300 MHz) δ 7.89 (d, J=8.7 Hz, 2H), 7.82 (d, J=16.8 Hz, 1H), 7.59 (d, J=8.7 Hz, 2H), 7.40-7.37 (m, 2H), 7.20 (dd, J=2.1, 8.1 Hz, 1H), 6.78 (d, J=16.8 Hz, 1H), 1.72 (s, 4H), 1.30 (s, 6H), 1.28 (s, 6H);

$^1$H NMR for Compound 3b ($CD_3OD$, 300 MHz) δ 7.95 (d, J=8.7 Hz, 2H), 7.48 (d, J=8.7 Hz, 2H), 7.41 (d, J=8.0 Hz, 1H), 7.23 (d, J=8.0 Hz, 1H), 7.16 (d, J=16.2 Hz, 1H), 7.06 (dd, J=1.8, 8.1 Hz, 1H), 6.49 (d, J=16.2 Hz, 1H), 1.73 (s, 4H), 1.31 (s, 6H), 1.28 (s, 6H).

General Procedure D Ethyl 3-fluoro-4-[3-oxo-3-(5,5,8,8-tetramethyl-5,6,7,8-tetrahydro-naphthalen-2-yl)-propenyl]-benzoate (Compound 4)

4-Bromo-2-fluoro-benzaldehyde (available from Aldrich, 1.32 g, 6.52 mmol) was added to a solution of 1-(5,5,8,8-tetramethyl-5,6,7,8-tetrahydro-naphthalen-2-yl)-ethanone (Compound 1, 1.50 g, 6.52 mmol) in 10 mL of 1 N NaOH and 20 mL of methanol. After stirring at room temperature for 18 h, the reaction mixture was extracted with ethyl acetate (3×10 mL). The combined organic layer was washed with brine (1×10 mL), dried ($MgSO_4$) and concentrated at reduced pressure to give a crude white solid. The solid was then transferred to a sealed tube containing 1,3-bis(diphenylphosphino)propane (214 mg, 0.52 mmol) and palladium acetate (146 mg, 0.65 mmol) in 20 mL dimethylformamide (DMF), 5 mL of triethylamine (TEA) and 10 mL of anhydrous ethanol. After bubbling the solution with carbon monoxide for 20 min, the tube was sealed and heated at 85° C. for 48 h. The reaction mixture was then cooled to room temperature and the solvent was removed in vacuo. The residue was dissolved in 30 mL dichloromethane, washed with 1N HCl (2×20 mL) and brine (2×20 mL). The organic layer was then dried ($MgSO_4$) and concentrated at reduced pressure. Purification by flash chromatography (90:10 hexane/ethyl acetate) afforded ester 4 (0.78 g, 29% yield) as a colorless oil:

$^1$H NMR ($CDCl_3$, 300 MHz) δ 7.99 (d, J=1.8 Hz, 1H), 7.87-7.64 (m, 6H), 7.42 (d, J=8.4 Hz, 1H), 4.39 (q, J=7.2 Hz, 2H), 1.71 (s, 4H), 1.37 (t, J=7.2 Hz, 3H), 1.33 (s, 6H), 1.30 (s, 6H).

General Procedure E E-3-Fluoro-4-[3-hydroxyimino-3-(5,5,8,8-tetramethyl-5,6,7,8-tetrahydro-naphthalen-2-yl)-propenyl]-benzoic acid (Compound 5a) and Z-3-fluoro-4-[3-hydroxyimino-3-(5,5,8,8-tetramethyl-5,6,7,8-tetrahydro-naphthalen-2-yl)-propenyl]-benzoic acid (Compound 5b)

To a solution of ethyl 3-fluoro-4-[3-oxo-3-(5,5,8,8-tetramethyl-5,6,7,8-tetrahydro-naphthalen-2-yl)-propenyl]-benzoate (Compound 4, 390 mg, 0.96 mmol) in 5 mL of EtOH was added hydroxylamine hydrochloride (133 mg, 1.92 mmol) and pyridine (160 mg, 2.02 mmol). The reaction mixture was then heated at reflux for 6 h. After cooling to room temperature, the solvent was removed in vacuo and the residue was taken up in water. The aqueous layer was adjusted to pH=4-5 with 1 N HCl and extracted with ethyl acetate (3×10 mL). The organic layers were combined and washed with water (2×10 mL) and brine (1×10 mL), dried ($MgSO_4$) and concentrated at reduced pressure. The residue was then dissolved in 5 mL of EtOH and 1 mL of 1N LiOH was added. After stirring at room temperature for 4 h, the solvent was removed at reduced pressure. The residue was then dissolved in water, acidified with 2N HCl and extracted with ethyl acetate (3×5 mL). The extract was washed with brine (1×5 mL), dried ($MgSO_4$) and concentrated at reduced pressure. Recrystallization with acetonitrile yielded Compound 5a (90 mg, 24% yield) as a white solid and with chloroform/hexane gave Compound 5b (65 mg, 17% yield) as a white solid, respectively:

$^1$H NMR for Compound 5a ($CD_3OD$, 300 MHz) δ 7.80 (d, J=16.5 Hz, 1H), 7.75-7.67 (m, 2H), 7.59 (dd, J=1.5, 11.0 Hz, 1H), 7.33-7.29 (m, 2H), 7.13 (dd, J=2.1, 8.1 Hz, 1H), 6.86 (d, J=16.5 Hz, 1H), 1.64 (s, 4H), 1.22 (s, 6H), 1.20 (s, 6H);

$^1$H NMR for Compound 5b ($CD_3OD$, 300 MHz) δ 6 7.81 (dd, J=1.5, 8.5 Hz, 1H), 7.72-7.64 (m, 2H), 7.44 (d, J=8.0 Hz, 1H), 7.28-7.25 (m, 2H), 7.10 (dd, J=2.0, 8.5 Hz, 1H), 6.65 (d, J=17.0 Hz, 1H), 1.76 (s, 4H), 1.34 (s, 6H), 1.31 (s, 6H).

Reaction Scheme 5
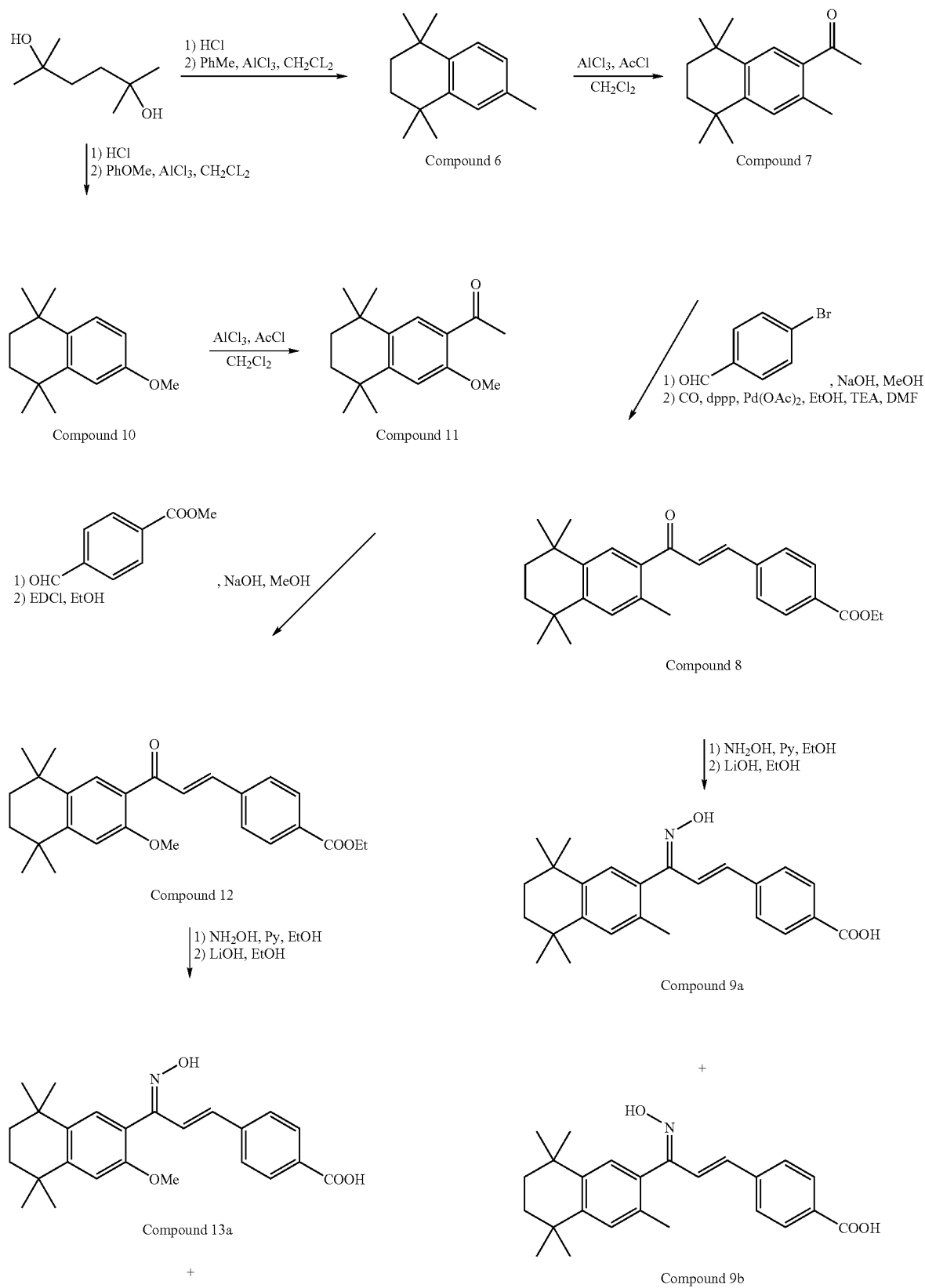

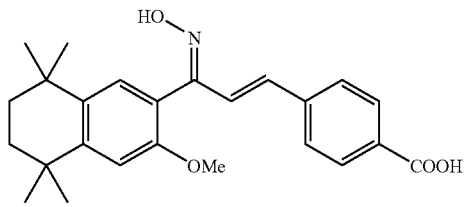

Compound 13b

1,1,4,4,6-Pentamethyl-1,2,3,4-tetrahydro-naphthalene (Compound 6)

2,3-Dimethyl-butane-2,3-diol (20.0 g, 0.14 mol) was added portionwise to 100 mL of conc. HCl at room temperature. After stirring for 1 h, a viscous white slurry was formed. The mixture was cooled with an ice bath, 50 mL of ice-water was added, the mixture filtered and dried at reduced pressure. The residue was then dissolved in a mixture of dichloromethane (100 mL) and toluene (25.8 g, 0.28 mol). Aluminum chloride (200 mg 1.50 mmol) was added slowly and the mixture was stirred at room temperature for 3 h. The mixture was then poured to 100 mL of ice-water, extracted with dichloromethane (3×10 mL), washed with saturated sodium bicarbonate (1×10 mL) and brine (1×110 mL). After the extract was dried (MgSO$_4$) and concentrated at reduced pressure, high-vacuum distillation of the crude afforded the title compound (Compound 6, 21.5 g, 76% yield) as a colorless oil:

$^1$H NMR (CDCl$_3$, 300 MHz) δ 7.20 (d, J=7.7 Hz, 1H), 7.12 (s, 1H), 6.95 (d, J=7.7 Hz, 1H), 2.30 (s, 3H), 1.67 (s, 4H), 1.27 (s, 6H), 1.26 (s, 6H).

1-(3,5,5,8,8-Pentamethyl-5,6,7,8-tetrahydro-naphthalen-2-yl)-ethanone (Compound 7)

Following General Procedure A and using 1,1,4,4,6-pentamethyl-1,2,3,4-tetrahydro-naphthalene (Compound 6, 1.0 g, 4.95 mmol) as the starting material yielded the title compound (1.2 g, 98% yield) as a white solid:

$^1$H NMR (CDCl$_3$, 300 MHz) δ 7.66 (s, 1H), 7.14 (s, 1H), 2.57 (s, 3H), 2.49 (s, 3H), 1.68 (s, 4H), 1.30 (s, 6H), 1.28 (s, 6H).

Ethyl 4-[3-oxo-3-(3,5,5,8,8-pentamethyl-5,6,7,8-tetrahydro-naphthalen-2-yl)-propenyl]-benzoate (Compound 8)

Following General Procedure D and using 1-(3,5,5,8,8-pentamethyl-5,6,7,8-tetrahydro-naphthalen-2-yl)-ethanone (Compound 7, 720 mg, 2.95 mmol) as the starting material the title compound (244 mg, 20% yield) was obtained as a white solid:

$^1$H NMR (CDCl$_3$, 300 MHz) δ 8.07 (d, J=8.7 Hz, 2H), 7.66-7.49 (m, 5H), 7.19 (s, 1H), 4.39 (q, J=7.2 Hz, 2H), 2.43 (s, 3H), 1.70 (s, 4H), 1.38 (t, J=7.2 Hz, 3H), 1.30 (s, 6H), 1.29 (s, 6H).

E-4-[3-Hydroxyimino-3-(3,5,5,8,8-pentamethyl-5,6,7,8-tetrahydro-naphthalen-2-yl)-propenyl]-benzoic acid (Compound 9a) and Z-4-[3-hydroxyimino-3-(3,5,5,8,8-pentamethyl-5,6,7,8-tetrahydro-naphthalen-2-yl)-propenyl]-benzoic acid (Compound 9b)

Following General Procedure E and using ethyl 4-[3-oxo-3-(3,5,5,8,8-pentamethyl-5,6,7,8-tetrahydro-naphthalen-2-yl)-propenyl]-benzoate (Compound 8, 244 mg, 0.61 mmol) as the starting material Compound 9a (72 mg, 30% yield) and Compound 9b (17 mg, 7% yield) were obtained as white solids. Separation of the E- and Z-isomers were achieved at the ester intermediates by medium pressure liquid chromatography (MPLC) (80:20 hexane/ethyl acetate) prior to saponification. Each acid was finally purified by recrystallization in acetonitrile:

$^1$H NMR for Compound 9a (acetone-d$_6$, 300 MHz) δ 8.04-7.95 (m, 3H), 7.64 (d, J=8.7 Hz, 2H), 7.22 (d, J=20.0 Hz, 1H), 6.50 (d, J=16.5 Hz, 1H), 2.20 (s, 3H), 1.72 (s, 4H), 1.31 (s, 6H), 1.28 (s, 6H);

$^1$H NMR for Compound 9b (acetone-d$_6$, 500 MHz) δ 8.00 (d, J=8.5 Hz, 2H), 7.58 (d, J=8.5 Hz, 2H), 7.29 (d, J=16.5 Hz, 1H), 7.30 (s, 1H), 7.05 (s, 1H), 6.36 (d, J=16.5 Hz, 1H), 2.17 (s, 3H), 1.74 (s, 4H), 1.34 (s, 6H), 1.29 (s, 6H).

6-Methoxy-1,1,4,4-tetramethyl-1,2,3,4-tetrahydro-naphthalene (Compound 10)

2,3-Dimethyl-butane-2,3-diol (10.0 g, 0.07 mol) was added portionwise to 100 mL of conc. HCl at room temperature. After stirring for 1 h, a viscous white slurry was formed. The mixture was cooled with an ice bath, 50 mL of ice-water was added, the mixture filtered and dried at reduced pressure. The residue was then dissolved in a mixture of dichloromethane (100 mL) and anisole (15.1 g, 0.14 mol). Aluminum chloride (100 mg 0.75 mmol) was added slowly at 0° C. and the mixture was stirred at room temperature for 12 h. The mixture was then poured to 100 mL of ice-water, extracted with dichloromethane (3×10 mL), washed with saturated sodium bicarbonate (1×10 mL) and brine (1×10 mL). The extract was dried (MgSO$_4$) and concentrated at reduced pressure. Purification by flash chromatography (95:5 hexane/ethyl acetate) afforded the title compound (11.8 g, 77% yield) as a white solid:

$^1$H NMR (CDCl$_3$, 300 MHz) δ 7.22 (d, J=7.7 Hz, 1H), 6.82 (dd, J=2.4, 7.7 Hz, 1H), 6.70 (d, J=2.4 Hz, 1H), 3.79 (s, 3H), 1.67 (s, 4H), 1.27 (s, 6H), 1.26 (s, 6H).

1-(3-Methoxy-5,5,8,8-tetramethyl-5,6,7,8-tetrahydro-naphthalen-2-yl)-ethanone (Compound 11)

Following General Procedure A and using 6-methoxy-1,1,4,4-tetramethyl-1,2,3,4-tetrahydro-naphthalene (Compound 10, 2.0 g, 9.17 mmol) as the starting material the title compound (2.3 g, 96% yield) was obtained as a white solid:

$^1$H NMR (CDCl$_3$, 300 MHz) δ 7.72 (s, 1H), 6.84 (s, 1H), 3.88 (s, 3H), 2.61 (s, 3H), 1.69 (s, 4H), 1.30 (s, 6H), 1.28 (s, 6H).

Ethyl 4-[3-(3-methoxy-5,5,8,8-tetramethyl-5,6,7,8-tetrahydro-naphthalen-2-yl)-3-oxo-propenyl]-benzoate (Compound 12)

Methyl 4-formylbenzoate (185 mg, 1.13 mmol) was added to a solution of 1-(3-methoxy-5,5,8,8-tetramethyl-5,6,7,8-tetrahydro-naphthalen-2-yl)-ethanone (Compound 11, 293 mg, 1.13 mmol) in 5 mL of 1 N NaOH and 10 mL of methanol. After stirring at room temperature for 18 h, the reaction mixture was extracted with ethyl acetate (3×10 mL). The combined organic layer was washed with brine (1×10 mL), dried (MgSO$_4$) and concentrated at reduced pressure. The residue was then added to a solution of ethanol (520 mg, 11.30 mmol), 1-(3-dimethylaminopropyl)-3-ethylcarbodiimide hydrochloride (EDCI) (433 mg, 2.26 mmol) and N,N-dimethylaminopyridine (DMAP) (13 mg, 0.11 mmol) in 5 mL of dichloromethane. After stirring at room temperature for 8 h, water (10 mL) was added and the mixture was extracted with ethyl acetate (3×5 mL), washed with brine (1×5 mL), dried (MgSO$_4$) and concentrated at reduced pressure. Purification by flash chromatography (80:20 hexane/ethyl acetate) afforded the title compound (153 mg, 32% yield) as a colorless oil:

$^1$H NMR (CDCl$_3$, 300 MHz) δ 8.04 (d, J=8.1 Hz, 2H), 7.70-7.51 (m, 5H), 6.88 (s, 1H), 4.38 (q, J=7.0 Hz, 2H), 3.90 (s, 3H), 1.69 (s, 4H), 1.40 (t, J=7.0 Hz, 3H), 1.32 (s, 6H), 1.28 (s, 6H).

E-4-[3-Hydroxyimino-3-(3-methoxy-5,5,8,8-tetramethyl-5,6,7,8-tetrahydro-naphthalen-2-yl)-propenyl]-benzoic acid (Compound 13a) and Z-4-[3-hydroxyimino-3-(3-methoxy-5,5,8,8-tetramethyl-5,6,7,8-tetrahydro-naphthalen-2-yl)-propenyl]-benzoic acid (Compound 13b)

Following General Procedure E and using ethyl 4-[3-(3-methoxy-5,5,5,8,8-tetramethyl-5,6,7,8-tetrahydro-naphthalen-2-yl)-3-oxo-propenyl]-benzoate (Compound 12, 244 mg, 0.61 mmol) as the starting material afforded Compound 13a (42 mg, 30% yield) and Compound 13b (13 mg, 7% yield) as white solids. Separation of the E- and Z-isomers was achieved at the ester intermediates by medium pressure liquid chromatography (MPLC) (80:20 hexane/ethyl acetate) prior to saponification. Each acid was finally purified by recrystallization in acetonitrile:

$^1$H NMR for Compound 13a (acetone-d$_6$, 500 MHz) δ 7.90 (d, J=8.5 Hz, 2H), 7.66 (d, J=16.5 Hz, 1H), 7.52 (d, J=8.5 Hz, 2H), 7.09 (s, 1H), 6.88 (s, 1H), 6.39 (d, J=16.5 Hz, 1H), 3.64 (s, 3H), 1.60 (s, 4H), 1.25 (s, 6H), 1.18 (s, 6H);

$^1$H NMR for Compound 13b (acetone-d$_6$, 500 MHz) δ7.86 (d, J=8.5 Hz, 2H), 7.40 (d, J=8.5 Hz, 2H), 7.09 (d, J=16.0 Hz, 1H), 6.92 (s, 1H), 6.88 (s, 1H), 6.28 (d, J=16.0 Hz, 1H), 3.64 (s, 3H), 1.63-1.58 (m, 4H), 1.23 (s, 6H), 1.15 (s, 6H).

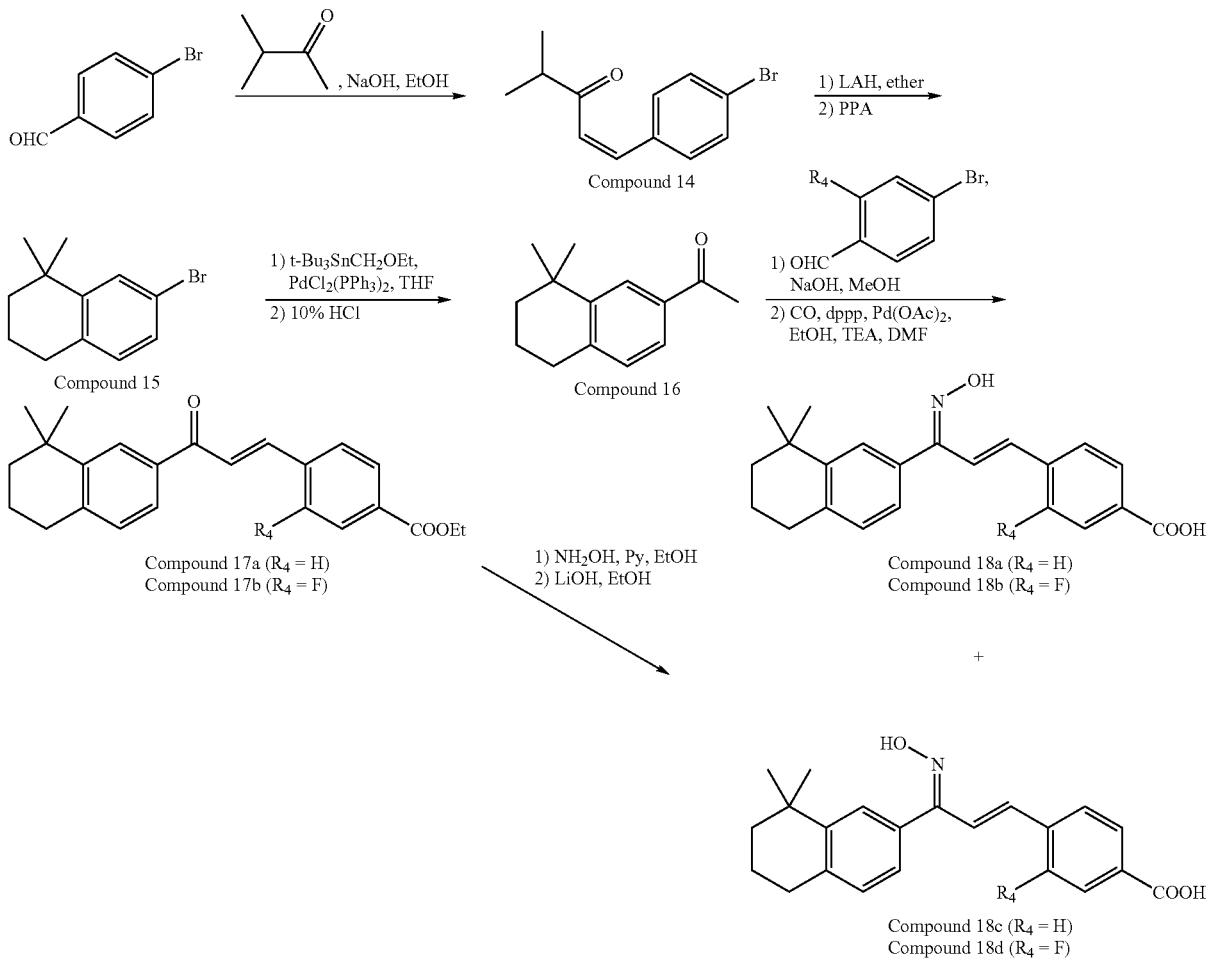

Reaction Scheme 6

1-(4-Bromo-phenyl)-4-methyl-pent-1-en-3-one (Compound 14)

4-Bromo-benzaldehyde (available from Aldrich, 10.0 g, 54.3 mmol) was added to a solution of 3-methyl-butan-2-one (available from Aldrich, 4.7 g, 54.7 mmol) in 10 mL of 10% NaOH$_{(aq)}$ and 20 mL of ethanol. After stirring at room temperature for 3 h, the reaction mixture was diluted with water (50 mL) and extracted with diethyl ether (3×20 mL). The organic layer was then washed with brine (1×5 mL), dried (MgSO$_4$) and concentrated at reduced pressure. Purification by flash chromatography (95:5 hexane/ethyl acetate) gave the title compound (7.98 g, 58% yield) as a light yellow oil:
$^1$H NMR (CDCl$_3$, 300 MHz) δ 7.54 (d, J=16.2 Hz, 1H), 7.53 (d, J=8.7 Hz, 2H), 7.42 (d, J=8.7 Hz, 2H), 6.80 (d, J=16.2 Hz, 2H), 2.93-2.87 (m, 1H), 1.18 (d, J=6.9 Hz, 6H).

7-Bromo-1,1-dimethyl-1,2,3,4-tetrahydro-naphthalene (Compound 15)

To a solution of 1-(4-bromo-phenyl)-4-methyl-pent-1-en-3-one (Compound 14, 7.98 g, 31.7 mmol) in 20 mL diethyl ether at 0° C. was slowly added lithium aluminum hydride (LAH) (1.20 g, 38.0 mmol). After stirring for one hour and subsequent warming to room temperature the reaction was quenched by 2 mL of saturated ammonium chloride solution at 0° C. with an ice bath and dried over anhydrous MgSO$_4$. Solid was removed by filtration and the filtrate was concentrated at reduced pressure to obtain a crude colorless oil. 5 g of polyphosphoric acid (PPA) was then added to the crude oil and the mixture was heated at 120° C. for 15 min. After cooling to room temperature, the mixture was taken up in water (100 mL), extracted with diethyl ether (3×15 mL), washed with brine (1×15 mL), dried (MgSO$_4$) and concentrated at reduced pressure. Purification by flash chromatography (hexane) afforded the title compound (6.70 g, 89% yield) as a light yellow oil:
$^1$H NMR (CDCl$_3$, 300 MHz) δ 735 (d, J=2.1 Hz, 1H), 7.09 (dd, J=1.8, 8.1 Hz, 1H), 6.83 (d, J=8.4 Hz, 1H), 2.60 (t, J=6 Hz, 2H), 1.75-1.59 (m, 2H), 1.56-1.47 (m, 2H), 1.19 (s, 6H).

General Procedure F 1-(8,8-Dimethyl-5,6,7,8-tetrahydro-naphthalen-2-yl)-ethanone (Compound 16)

A solution of 7-bromo-1,1-dimethyl-1,2,3,4-tetrahydro-naphthalene (Compound 15, 1.20 g, 5.94 mmol) in 20 ml of THF was first degassed by bubbling with argon for 30 min. Tributyl(1-ethoxyvinyl)tin (4.29 g, 11.88 mmol) and PdCl$_2$(PPh$_3$)$_2$ (422 mg, 0.60 mmol) were added. After stirring at 80° C. for 18 h, the mixture was cooled to room temperature and 3 mL of 10% HCl was added. The mixture was then stirred for another 30 min, then extracted with ethyl acetate (3×10 mL). The combined organic layer was washed with brine (1×10 mL), dried (MgSO$_4$) and concentrated at reduced pressure. Purification by flash chromatography (80:20 hexane/ethyl acetate) afforded the title compound (669 mg, 56% yield) as a colorless oil:
$^1$H NMR (CDCl$_3$, 300 MHz) δ 7.95 (d, J=2.1 Hz, 1H), 7.63 (dd, J=1.8, 8.1 Hz, 1H), 7.12 (d, J=7.8 Hz, 1H), 2.80 (t, J=6.3 Hz, 2H), 2.57 (s, 3H), 1.84-1.80 (m, 2H), 1.70-1.58 (m, 2H), 1.31 (s, 6H).

Ethyl 4-[3-(8,8-dimethyl-5,6,7,8-tetrahydro-naphthalen-2-yl)-3-oxo-propenyl]-benzoate (Compound 17a)

Following General Procedure D and using 1-(8,8-dimethyl-5,6,7,8-tetrahydro-naphthalen-2-yl)-ethanone (Compound 16, 336 mg, 1.66 mmol) and 4-bromo-benzaldehyde as the starting materials the title compound (250 mg, 42% yield) was obtained as a yellow solid:
$^1$H NMR (CDCl3, 300 MHz) δ 8.09 (d, J=8.1 Hz, 2H), 8.02 (d, J=1.8 Hz, 1H), 7.79 (d, J=16.0 Hz, 1H), 7.73-7.67 (m, 3H), 7.58 (d, J=16.0 Hz, 1H), 7.16 (d, J=8.4 Hz, 1H), 4.39 (q, J=7.2 Hz, 2H), 2.84 (t, J=6.3 Hz, 2H), 1.87-1.80 (m, 2H), 1.72-1.68 (m, 2H), 1.41 (t, J=7.2 Hz, 3H), 1.34 (s, 6H).

Ethyl 4-[3-(8,8-dimethyl-5,6,7,8-tetrahydro-naphthalen-2-yl)-3-oxo-propenyl]-3-fluoro-benzoate (Compound 17b)

Following General Procedure D and using 1-(8,8-dimethyl-5,6,7,8-tetrahydro-naphthalen-2-yl)-ethanone (Compound 16, 333 mg, 1.65 mmol) as the starting material the title compound (400 mg, 64% yield) was obtained as a yellow solid:
$^1$H NMR (CDCl$_3$, 300 MHz) δ8.01 (d, J=1.8 Hz, 1H), 7.88-7.65 (m, 6H), 7.17 (d, J=8.1 Hz, 1H), 4.39 (q, J=7.2 Hz, 2H), 2.85 (t, J=6.3 Hz, 2H), 1.85-1.82 (m, 2H), 1.72-1.68 (m, 2H), 1.42 (t, J=7.2 Hz, 3H), 1.34 (s, 6H)

E-4-[3-(8,8-Dimethyl-5,6,7,8-tetrahydro-naphthalen-2-yl)-3-hydroxyimino-propenyl]-benzoic acid (Compound 18a) and Z-4-[3-(8,8-dimethyl-5,6,7,8-tetrahydro-naphthalen-2-yl)-3-hydroxyimino-propenyl]-benzoic acid (Compound 18c)

Following General Procedure E and using ethyl 4-[3-(8,8-dimethyl-5,6,7,8-tetrahydro-naphthalen-2-yl)-3-oxo-propenyl]-benzoate (Compound 17a, 250 mg, 0.69 mmol) as the starting material Compound 18a (37 mg, 15% yield) and Compound 18c (21 mg, 9% yield) were obtained as white solids. Separation of the E- and Z-isomers was achieved at the ester intermediates by medium pressure liquid chromatography (MPLC) (80:20 hexane/ethyl acetate) prior to saponification. After saponification each isomer was finally purified by recrystallization in acetonitrile:
$^1$H NMR for Compound 18a (acetone-d$_6$, 300 MHz) δ 7.92 (d, J=8.1 Hz, 2H), 7.73 (d, J=16.5 Hz, 1H), 7.58 (d, J=8.1 Hz, 2H), 7.37 (d, J=1.8 Hz, 1H), 7.08 (dd, J=1.8, 8.1 Hz, 1H), 6.96 (d, J=7.8 Hz, 1H), 6.75 (d, J=16.5 Hz, 1H), 2.67 (t, J=6.3 Hz, 2H), 1.72-1.68 (m, 2H), 1.59-1.55 (m, 2H), 1.17 (s, 6H).
$^1$H NMR for Compound 18c (acetone-d$_6$, 300 MHz) δ 7.86 (d, J=8.1 Hz, 2H), 7.44 (d, J=8.1 Hz, 1H), 7.19-6.90 (m, 4H), 6.43 (d, J=16.5 Hz, 1H), 2.67 (t, J=6.3 Hz, 2H), 1.73-1.67 (m, 2H), 1.59-1.56 (m, 2H), 1.17 (s, 6H).

E-4-[3-(8,8-Dimethyl-5,6,7,8-tetrahydro-naphthalen-2-yl)-3-hydroxyimino-propenyl]-3-fluoro-benzoic acid (Compound 18b) and Z-4-[3-(8,8-dimethyl-5,6,7,8-tetrahydro-naphthalen-2-yl)-3-hydroxyimino-propenyl]-3-fluoro-benzoic acid (Compound 18d)

Following General Procedure E and using ethyl 4-[3-(8,8-dimethyl-5,6,7,8-tetrahydro-naphthalen-2-yl)-3-oxo-propenyl]-3-fluoro-benzoate (Compound 17b, 400 mg, 1.05 mmol) as the starting material Compound 18b (64 mg, 17% yield) and Compound 18d (45 mg, 12% yield) were obtained as white solids. Separation of the E- and Z-isomers was achieved at the ester intermediates by medium pressure liquid chromatography (MPLC) (80:20 hexane/ethyl acetate) prior to saponification. After saponification each isomer was finally purified by recrystallization in acetonitrile:

$^1$H NMR for Compound 18b (acetone-$d_6$, 300 MHz) δ 7.97-7.88 (m, 3H), 7.73 (dd, J=1.5, 11.7 Hz, 1H), 7.51 (d, J=1.8 Hz, 1H), 7.22 (dd, J=1.8, 7.8 Hz, 1H), 7.11 (d, J=7.5 Hz, 1H), 6.99 (d, J=16.2 Hz, 1H), 2.80 (t, J=6.3 Hz, 2H), 1.86-1.80 (m, 214), 1.73-1.69 (m, 2H), 1.30 (s, 6H);

$^1$H NMR for Compound 18d (acetone-$d_6$, 300 MHz) δ 7.77-7.72 (m, 2H), 7.56 (dd, J=1.5, 12.0 Hz, 1H), 7.18 (d, J=16.3 Hz, 1H), 7.03-6.93 (m, 3H), 6.58 (d, J=16.3 Hz, 1H), 2.68 (t, J=6.3 Hz, 2H), 1.83-1.68 (m, 2H), 1.61-1.57 (m, 2H), 1.18 (s, 6H).

with brine (1×5 mL), dried (MgSO$_4$) and concentrated at reduced pressure. Purification by flash chromatography (hexane) afforded the title compound (445 mg, 90% yield) as a light yellow oil:

$^1$H NMR (CDCl$_3$, 300 MHz) δ 7.25-7.19 (m, 3H), 2.75 (t, J=6.0 Hz, 2H), 1.81-1.79 (m, 2H), 1.70-1.62 (m, 2H), 1.26 (s, 6H).

1-(5,5-Dimethyl-5,6,7,8-tetrahydro-naphthalen-2-yl)-ethanone (Compound 20)

Following General Procedure F and using 6-bromo-1,1-dimethyl-1,2,3,4-tetrahydro-naphthalene (Compound 19, 445 mg, 1.87 mmol) as the starting material the title compound was obtained (240 mg, 64% yield) as a white solid:

$^1$H NMR (CDCl$_3$, 300 MHz) δ 7.64-7.56 (m, 3H), 7.45 (d, J=16.0 Hz, 1H), 7.32 (d, J=8.1 Hz, 1H), 2.75 (t, J=6.0 Hz, 2H), 2.60 (s, 3H), 1.94-1.83 (m, 2H), 1.82-1.74 (m, 2H), 1.38 (s, 6H).

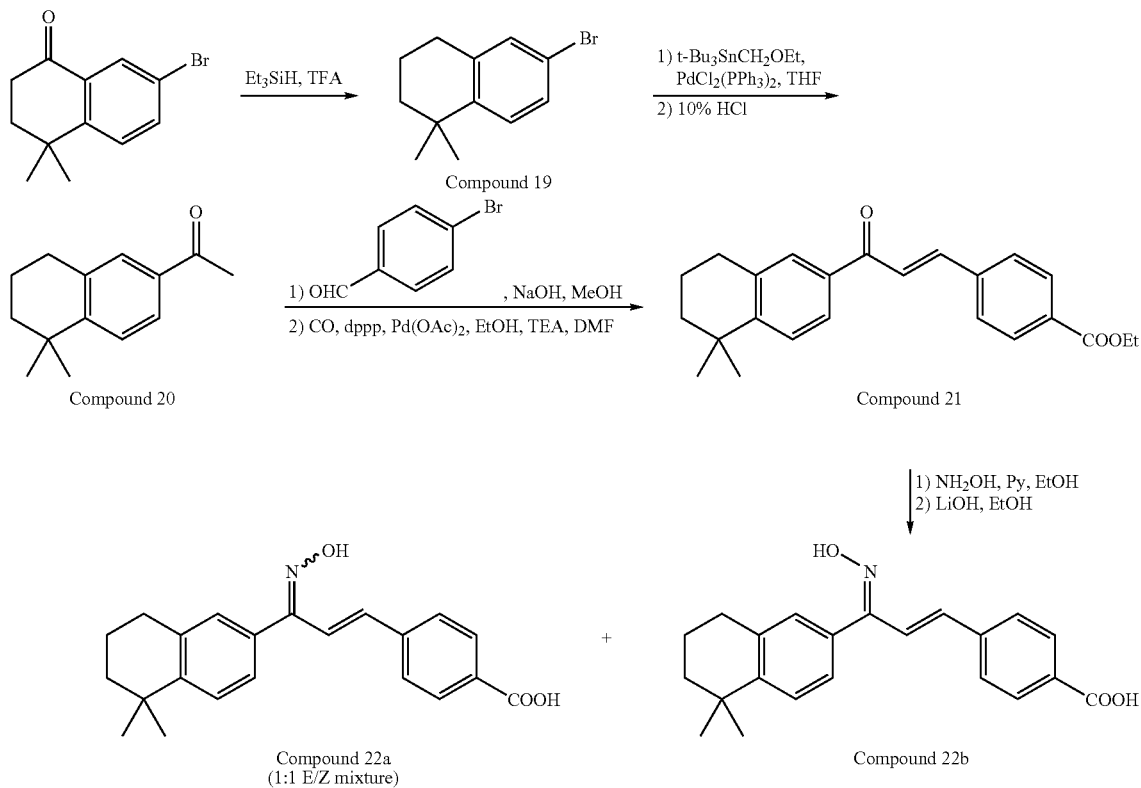

6-Bromo-1,1-dimethyl-1,2,3,4-tetrahydro-naphthalene (Compound 19)

To a solution of 7-bromo-4,4-dimethyl-3,4-dihydro-2H-naphthalen-1-one (prepared according to the procedures published in Journal of Medicinal Chemistry 1995, 38, 4764-7) (525 mg, 2.08 mmol) in 5 mL of trifluoroacetic acid (TFA) was added triethylsilane (2.41 g, 20.80 mmol). The mixture was then heated at reflux for 8 h. After cooling to room temperature, the reaction was quenched with 20 mL of ice-water mixture, extracted with diethyl ether (3×5 mL), washed Ethyl 4-[3-(5,5-dimethyl-5,6,7,8-tetrahydro-naphthalen-2-yl)-3-oxo-propenyl]-benzoate (Compound 21)

Following General Procedure D and using 1-(5,5-dimethyl-5,6,7,8-tetrahydro-naphthalen-2-yl)-ethanone (Compound 20, 240 mg, 1.19 mmol) and 4-bromo-benzaldehyde as the starting materials the title compound was obtained (80 mg, 19% yield) as a yellow oil:

$^1$H NMR (CDCl$_3$, 300 MHz) δ 8.07 (d, J=8.1 Hz, 2H), 7.82-7.80 (m, 2H), 7.78-7.70 (m, 3H), 7.59 (d, J=16.0 Hz,

1H), 7.46 (d, J=8.1 Hz, 1H), 4.40 (q, J=7.5 Hz, 2H), 2.86 (t, J=6.3 Hz, 2H), 1.86-1.82 (m, 2H), 1.72-1.68 (m, 2H) 1.41 (t, J=7.5 Hz, 3H), 1.31 (s, 6H).

4-[3-(5,5-Dimethyl-5,6,7,8-tetrahydro-naphthalen-2-yl)-3-hydroxyimino-propenyl]-benzoic acid (Compound 22a) and Z-4-[3-(5,5-dimethyl-5,6,7,8-tetrahydro-naphthalen-2-yl)-3-hydroxyimino-propenyl]-benzoic acid (Compound 22b)

Following General Procedure E and using ethyl 4-[3-(5,5-dimethyl-5,6,7,8-tetrahydro-naphthalen-2-yl)-3-oxo-propenyl]-benzoate (Compound 21, 80 mg, 0.22 mmol) as the starting material Compound 22a (22 mg, 29% yield) and Compound 22b (2 mg, 3% yield) were obtained as white solids. In this case only some Z-isomer was isolated from the E/Z mixture of ester intermediates by high performance liquid chromatography (HPLC) (90:10 hexane/ethyl acetate) prior to saponification. After saponification the Z isomer and the mixture of isomers was further purified by recrystallization in acetonitrile:

$^1$H NMR for Compound 22a (1:1 E/Z mixture) (CD$_3$OD, 300 MHz) δ 7.91-7.84 (m, 2H), 7.69 (d, J=16.5 Hz, 0.5H), 7.50 (d, J=8.1 Hz, 1H), 7.33-7.30 (m; 2H), 7.13-7.04 (m, 2H), 6.94 (d, J=7.8 Hz, 0.5 H), 6.70 (d, J=15.0 Hz, 0.5 H), 6.39 (d, J=15.0 Hz, 0.5 H), 2.69 (t, J=5.4 Hz, 2H), 1.74-1.77 (m, 2H), 1.63-1.61 (m, 2H), 1.24 (s, 6H);

$^1$H NMR for Compound 22b (CDCl$_3$, 300 MHz) δ 7.99 (d, J=8.1 Hz, 2H), 7.48 (d, J=8.1 Hz, 2H), 7.39. (d, J=7.8 Hz, 1H), 7.20-6.97 (m, 3H), 6.58 (d, J=16.2 Hz, 1H), 2.75 (t, J=6.0 Hz, 2H), 1.76-1.79(m, 2H), 1.65-1.63 (m, 2H), 1.26 (s, 6H).

Synthesis of Thiochroman Exemplary Compounds of the Invention

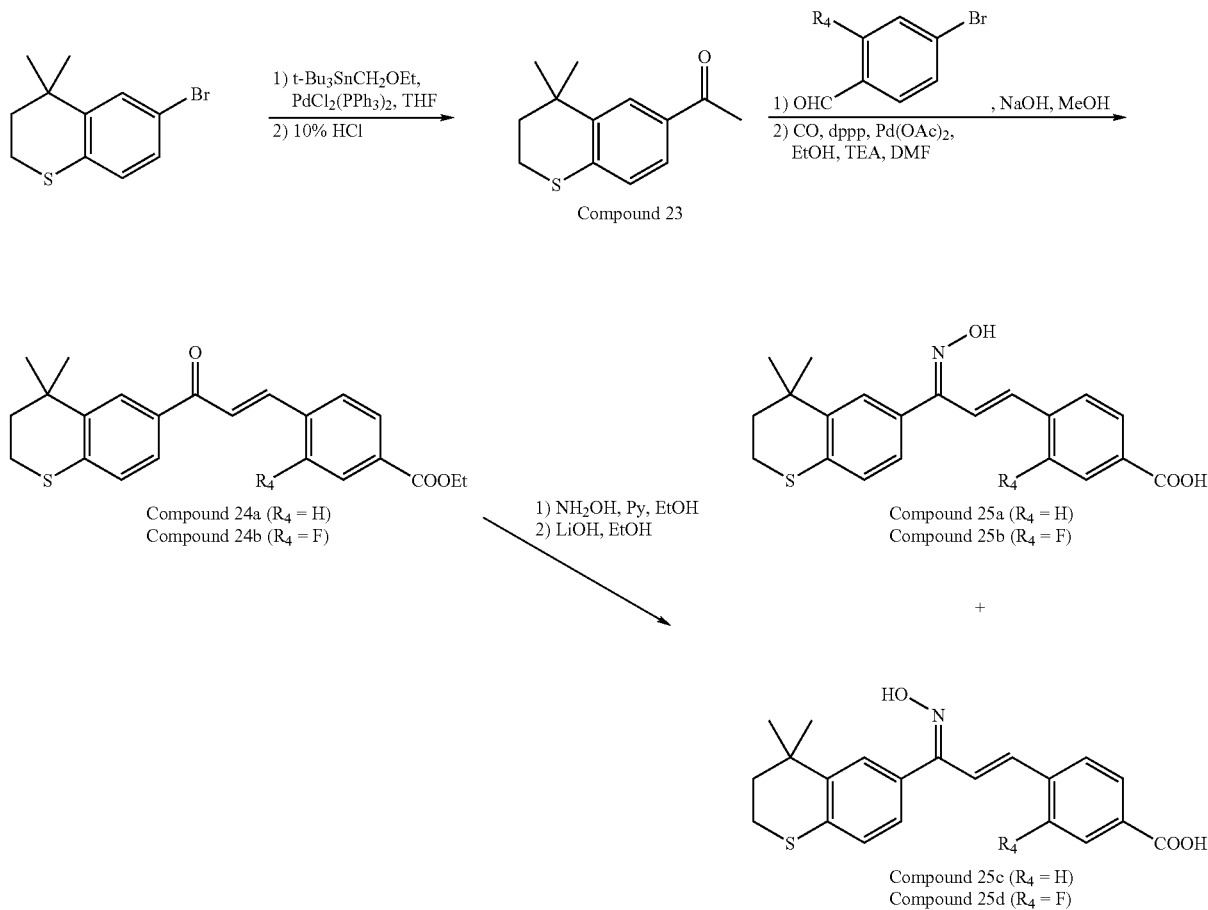

1-(4,4-Dimethyl-thiochroman-6-yl)-ethanone (Compound 23)

Following General Procedure F and using 6-bromo-4,4-dimethyl-thiochroman (prepared according to the procedures published in U.S. Pat. No. 4,895,868 (1990)) (1.0 g, 3.91 mmol) as the starting material the title compound was obtained (720 mg, 84% yield) as a colorless oil:

$^1$H NMR (CDCl$_3$, 300 MHz) δ 7.98 (d, J=1.8 Hz, 1H), 7.58 (dd, J=1.8, 8.1 Hz, 1H), 7.14 (d, J=8.1 Hz, 1H), 3.08-3.04 (m, 2H), 2.54 (s, 3H), 1.98-1.94 (m, 2H), 1.35 (s, 6H).

Ethyl 4-[3-(4,4-dimethyl-thiochroman-6-yl)-3-oxo-propenyl]-benzoate (Compound 24a)

Following General Procedure D and using 1-(4,4-dimethyl-thiochroman-6-yl)-ethanone (Compound 23, 385 mg, 1.75 mmol) and 4-bromo-benzaldehyde as the starting materials the title compound was obtained (295 mg, 44% yield) as a yellow oil:

$^1$H NMR (CDCl$_3$, 300 MHz) δ 8.09-8.06 (m, 3H), 7.79 (d, J=15.9 Hz, 1H), 7.68 (d, J=8.4 Hz, 2H), 7.56 (d, J=15.9 Hz, 1H), 7.26 (s, 1H), 7.20 (d, J=8.1 Hz, 1H), 4.40 (q, J=7.0 Hz, 2H), 3.10-3.06 (m, 2H), 2.00-1.96 (m, 2H), 1.39 (s, 6H), 1.25 (t, J=7.0 Hz, 3H).

Ethyl 4-[3-(4,4-dimethyl-thiochroman-6-yl)-3-oxo-propenyl]-3-fluoro-benzoate (Compound 24b)

Following General Procedure D and using 1-(4,4-dimethyl-thiochroman-6-yl)-ethanone (Compound 23, 335 mg, 1.52 mmol) as the starting -material the title compound was obtained (213 mg, 35% yield) as a yellow oil:

$^1$H NMR (CDCl$_3$, 300 MHz) δ 8.07 (d, J=2.1 Hz, 1H), 7.89-7.72 (m, 3H), 7.69-7.64 (m, 3H), 7.20 (d, J=8.1 Hz, 1H), 4.40 (q, J=7.2 Hz, 2H), 3.10-3.06 (m, 2H), 2.04-1.96 (m, 2H), 1.39 (s, 6H), 1.25 (t, J=7.2 Hz, 3H).

E-4-[3-(4,4-Dimethyl-thiochroman-6-yl)-3-hydroxy-imino-propenyl]-benzoic acid (Compound 25a) and Z-4-[3-(4,4-dimethyl-thiochroman-6-yl)-3-hydroxy-imino-propenyl]-benzoic acid (Compound 25c)

Following General Procedure E and using ethyl 4-[3-(4,4-dimethyl-thiochroman-6-yl)-3-oxo-propenyl]-benzoate (Compound 24a, 295 mg, 0.78 mmol) as the starting material Compound 25a (9 mg, 3% yield) and Compound 25c (11 mg, 4% yield) were obtained as white solids. Separation of the E- and Z-isomers was achieved at the ester intermediates by medium pressure liquid chromatography (MPLC) (80:20 hexane/ethyl acetate) prior to saponification. After saponification each isomer was finally purified by recrystallization in acetonitrile:

$^1$H NMR for Compound 25a (acetone-d$_6$, 300 MHz) δ 7.91 (d, J=8.0 Hz, 2H), 7.69 (d, J=17.0 Hz, 1H), 7.60 (d, J=8.0 Hz, 2H), 7.44 (d, J=2.0 Hz, 1H), 7.07 (dd, J=2.0, 8.5 Hz, 1H), 6.97 (d, J=8 Hz, 1H), 6.79 (d, J=17.0 Hz, 1H), 2.97-2.95 (m, 2H), 1.88-1.85 (m, 2H), 1. 22 (s, 6H);

$^1$H NMR for Compound 25c (acetone-d$_6$, 300 MHz) δ 7.87 (d, J=8.1 Hz, 2H), 7.48 (d, J=8.1 Hz, 1H), 7.27 (d, J=1.5 Hz, 1H), 7.10-6.91 (m, 3H), 6.46 (d, J=16.8 Hz, 1H), 3.01-2.83 (m, 2H), 1.98-1.92 (m, 2H), 1.23 (s, 6H).

E-4-[3-(4,4-Dimethyl-thiochroman-6-yl)-3-hydroxy-imino-propenyl]-3-fluoro-benzoic acid (Compound 25b) and Z-4-[3-(4,4-dimethyl-thiochroman-6-yl)-3-hydroxyimino-propenyl]-3-fluoro-benzoic acid (Compound 25d)

Following General Procedure E and using ethyl 4-[3-(4,4-dimethyl-thiochroman-6-yl)-3-oxo-propenyl]-3-fluoro-benzoate (Compound 24b, 213 mg, 0.54 mmol) as the starting material Compound 25b (40 mg, 19% yield) and Compound 25d (8 mg, 4% yield) were obtained as white solids. Separation of the E- and Z-isomers was achieved at the ester intermediates by medium pressure liquid chromatography (MPLC) (80:20 hexane/ethyl acetate) prior to saponification. After saponification each isomer was finally purified by recrystallization in acetonitrile:

$^1$H NMR for Compound 25b (acetone-d$_{6,\,300}$ MHz) δ 7.97-7.88 (m, 3H), 7.73 (dd, J=1.5, 11.7 Hz, 1H), 7.51 (d, J=1.8 Hz, 1H), 7.22 (dd, J=1.8, 7.8 Hz, 1H), 7.11 (d, J=7.5 Hz, 1H), 6.99 (d, J=16.2 Hz, 1H), 2.80 (t, J=6.3 Hz, 2H), 1.86-1.80 (m, 2H), 1.73-1.69 (m, 2H), 1.30 (s, 6H);

$^1$H NMR for Compound 25d (acetone-d$_6$, 300 MHz) δ 7.84-7.74 (m, 3H), 7.59 (d, J=12.3 Hz, 1H), 7.46 (d, J=1.8 Hz, 1H), 7.09 (dd, J=1.2, 7.8 Hz, 3H), 6.98 (d, J=8.1 Hz, 1H), 6.90 (d, J=16.8 Hz, 1H), 2.98-2.81 (m, 2H), 1.90-1.80 (m, 2H), 1.22 (s, 6H).

Synthesis of Tetrahydroquinoline Exemplary Compounds of the Invention

Reaction Scheme 9

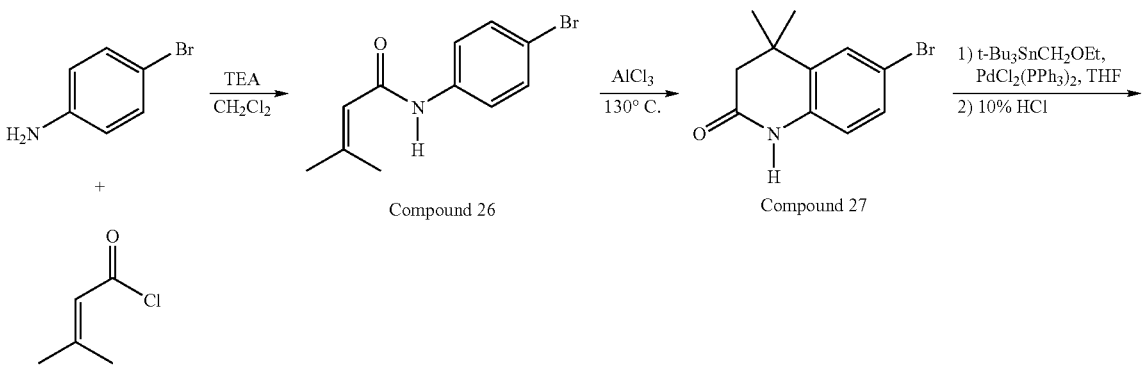

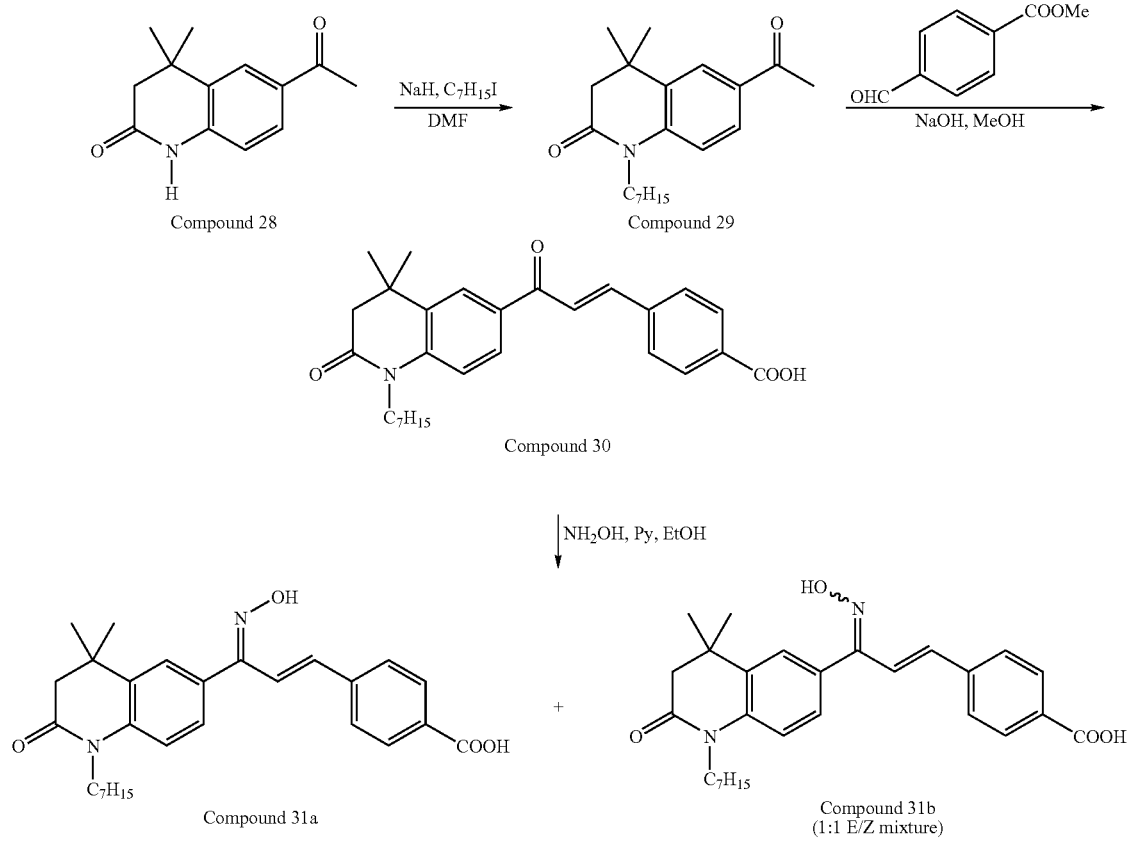

N-(4-Bromophenyl)-3-methylbut-2-enoic amide (Compound 26)

3,3-Dimethylacryloyl chloride (available from Aldrich, 4.16 g, 35.1 mmol) was slowly added to a solution of 4-bromoaniline (5.00 g, 29.2 mmol) in 25 mL of dichloromethane. After stirring at room temperature for 20 min triethylamine (2.5 mL) was added dropwise to the mixture. The resulting solution was stirred at room temperature for 3 h and poured to 100 mL of ice-water mixture. The organic layer was separated, washed with brine (2×20 mL), dried (MgSO$_4$) and concentrated at reduced pressure to give a yellow residue. Purification by flash chromatography (90:10 hexane/ethyl acetate) afforded the title compound (7.43 g, 100% yield) as a yellow solid: $^1$H NMR (CDCl$_3$, 300 MHz) δ 7.34 (s, 4H), 7.1 (bs, 1H), 5.69 (s, 1H), 2.23 (s, 3H), 1.91 (s, 3H).

6-Bromo-4,4-dimethyl-3 4-dihydro-1H-quinolin-2-one (Compound 27)

Aluminum chloride (5 g, 37.5 mmol) was added portionwise to N-(4-bromophenyl)-3-methylbut-2-enoic amide (Compound 26, 7.69 g, 30.0 mmol) in a 500 mL beaker at 130° C. over 1 h. The beaker was then cooled to 80° C. and another portion of aluminum chloride (1 g, 7.5 mmol) was added. After stirring at 80° C. for 0.5 h, the beaker was cooled with an ice-bath and ice was added slowly into the mixture. The resulting slurry was then extracted with ether (3×10 mL). The combined organic layer was washed with brine (1×10 mL), saturated NaHCO$_3$ (1×10 mL), dried (MgSO$_4$) and concentrated at reduced pressure. Purification by flash chromatography (75:25 hexane/ethyl acetate) gave the title compound (5.20 g, 68% yield) as a pale yellow solid:
$^1$H NMR (CDCl$_3$, 300 MHz) δ 7.40 (d, J=2.4 Hz, 1H), 7.31-7.27 (m, 2H), 6.65 (bs, 1H), 2.47 (s, 2H), 1.32 (s, 6H).

6-Acetyl-4,4-dimethyl-3,4-dihydro-1H-quinolin-2-one (Compound 28)

Following General Procedure F and using 6-bromo-4,4-dimethyl-3,4-dihydro-1H-quinolin-2-one (Compound 27,270 mg, 1.06 mmol) as the starting material the title compound was obtained (154 mg, 67% yield) as a white solid:
$^1$H NMR (CDCl$_3$, 300 MHz) δ 9.10 (bs, 1H), 7.95 (d, J=1.8 Hz, 1H), 7.80 (dd, J=1.8, 8.1 Hz, 1H), 6.89 (d, J=8.1 Hz, 1H), 2.59 (s, 3H), 2.54 (s, 2H), 1.38 (s, 6H).

N-Heptyl-6-acetyl-4,4-dimethyl-3,4-dihydro-1H-quinolin-2-one (Compound 29)

Sodium hydride (21.0 mg, 90.0 mmol) was slowly added into a solution of 6-acetyl-4,4-dimethyl-3,4-dihydro-1H-quinolin-2-one (Compound 28, 98.0 mg, 45.0 mmol) in 3 mL of DMF at 0° C. After stirring at 0° C. for 10 min, 1-iodoheptane (30.5 mg, 135.0 mmol) was added to the reaction mixture and the ice-bath was removed. The reaction mixture was allowed to stir for 2 h and then quenched with ice water. The resulting solution was then extracted with ether (3×10 mL), washed with brine (1×10 mL), dried (MgSO$_4$) and concentrated at reduced pressure. Purification by flash chromatography (75:25 hexane/ethyl acetate) yielded the title compound (93.6 mg, 66% yield) as a colorless oil:

$^1$H NMR (CDCl$_3$, 300 MHz) δ 7.93 (d, J=2.1 Hz, 1H), 7.86 (dd, J=2.1, 8.4 Hz, 1H), 7.06 (d, J=8.4 Hz, 1H), 4.01-3.96 (m, 2H), 2.59 (s, 3H), 2.53 (s, 2H), 1.66-1.59 (m, 3H), 1.39-1.24 (m, 13H), 0.90-0.86 (m, 3H).

4-[3-(1-Heptyl-4,4-dimethyl-2-oxo-1,2,3 4-tetrahydro-quinolin-6-yl)-3-oxo-propenyl]-benzoic acid (Compound 30)

Following General Procedure B and using N-heptyl-6-acetyl-4,4-dimethyl-3,4-dihydro-1H-quinolin-2-one (Compound 29, 330 mg, 1.05 mmol) as the starting materials the title compound (239 mg, 51% yield) was obtained as a yellow solid:

$^1$H NMR (acetone-d$_6$, 300 MHz) δ 11.35 (bs, 1H), 8.16-7.80 (m, 8H), 7.32 (d, J=9.0 Hz, 1H), 4.07-4.02 (m, 2H), 2.53 (s, 2H), 1.64-1.55 (m, 2H), 1.43-1.24 (m, 14H), 0.89-0.84 (m, 3H).

E-4-[3-(1-Heptyl-4,4-dimethyl-2-oxo-1,2,3,4-tetrahydro-quinolin-6-yl)-3-hydroxyimino-propenyl]-benzoic acid (Compound 31a) and 4-[3-(1-Heptyl-4,4-dimethyl-2-oxo-1,2,3,4-tetrahydro-quinolin-6-yl)-3-hydroxyimino-propenyl]-benzoic acid (Compound 31b)

Following General Procedure C and using 4-[3-(1-heptyl-4,4-dimethyl-2-oxo-1,2,3,4-tetrahydro-quinolin-6-yl)-3-oxo-propenyl]-benzoic acid (Compound 30, 56 mg, 0.13 mmol) as the starting material Compound 31a (11 mg, 18% yield) and Compound 31b (19 mg, 32% yield) were obtained as white solids. The E-isomer was obtained from the E/Z mixture by recrystallization in acetonitrile:

$^1$H NMR for Compound 31a (CDCl$_3$, 300 MHz) δ 7.76 (d, J=16.5 Hz, 1H), 7.53-7.48 (m, 3H), 7.39-7.31 (m, 2H), 7.08 (d, J=8.4 Hz, 1H), 6.74 (d, J=16.5 Hz, 1H), 3.92 (d, J=7.5 Hz, 2H), 2.45 (s, 2H), 1.62-1.45 (m, 2H), 1.30-1.23 (m, 14H), 0.82 (t, J=7.5 Hz, 3H);

$^1$H NMR for Compound 31b (1:1 E/Z mixture) (CDCl$_3$, 300 MHz) δ 8.01 (d, J=8.4 Hz, 2H), 7.97 (d, J=8.1 Hz, 1H), 7.83 (d, J=16.8 Hz, 0.5H), 7.60 (d, J=6.3 Hz, 1H), 7.50 (d, J=6.0 Hz, 1H), 7.48-7.17 (m, 2.5H), 6.82 (d, J=8.4 Hz, 0.5H), 6.51 (d, J=16.5 Hz, 0.5H), 4.02 (t, J=7.5 Hz, 4H), 2.52 (s, 2H), 1.67-1.62 (m, 2H), 1.39-1.30 (m, 14H), 0.89 (t, J 6.9 Hz, 3H).

Synthesis of Chroman Exemplary Compounds of the Invention

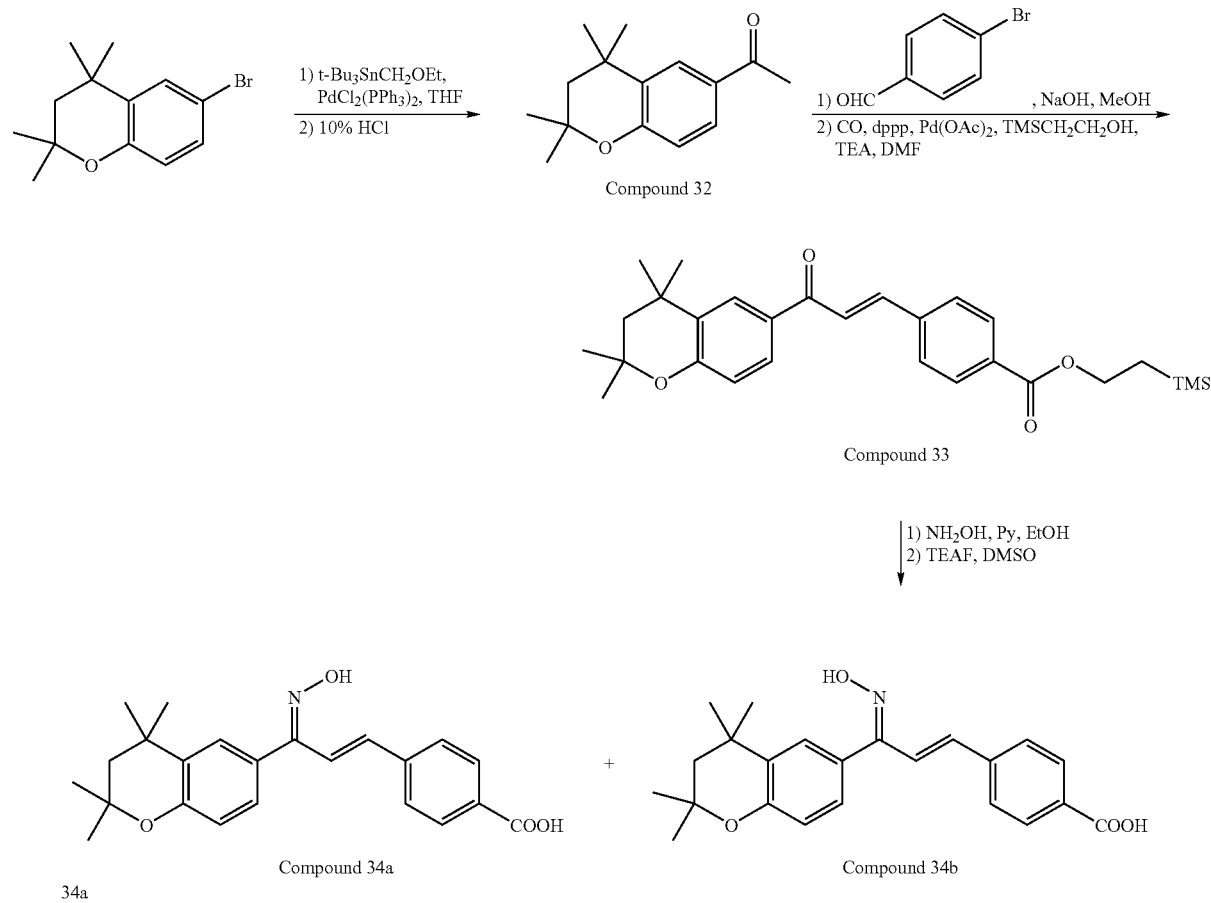

Reaction Scheme 10

1-(2,2,4,4-Tetramethyl-chroman-6-yl)-ethanone (Compound 32)

Following General Procedure F and using 6-bromo-4,4-tetramethyl-chroman prepared according to the procedure published in U.S. Pat. No. 6,303,785, incorporated herein by reference (450 mg, 1.68 mmol) as the starting material the title compound was obtained (237 mg, 61% yield) as a white solid:

$^1$H NMR (CDCl$_3$, 300 MHz) δ 7.96 (d, J=2.1 Hz, 1H), 6.80 (d, J=8.4 Hz, 1H), 6.68 (dd, J=2.1, 8.4 Hz, 1H), 2.60 (s, 3H), 1.86 (s, 2H), 1.38 (s, 6H), 1.36 (s, 6H).

2-Trimethylsilanyl-ethyl 4-[3-oxo-3-(2,2,4,4-tetramethyl-chroman-6-yl)-propenyl]-benzoate (33)

Following General Procedure D and using 1-(2,2,4,4-tetramethyl-chroman-6-yl)-ethanone (Compound 32, 195 mg, 0.84 mmol) and 4-bromo-benzaldehyde as the starting materials as well as trimethylsilanylethanol instead of ethanol for carboxylation, the title compound was obtained (155 mg, 40% yield) as a yellow oil:

$^1$H NMR (CDCl$_3$, 300 MHz) δ 8.04-8.00 (m, 1H), 7.80-7.44 (m, 4H), 6.83 (d, J=8.7 Hz, 1H), 4.44-4.39 (m, 2H), 1.84 (s, 2H), 1.37 (s, 6H), 1.34 (s, 6H), 0.00 (s, 9H).

General Procedure G E-4-[3-Hydroxyimino-3-(2,2,4,4-tetramethyl-chroman-6-yl)-propenyl]-benzoic acid (Compound 34a) and Z-4-[3-hydroxyimino-3-(2,2,4,4-tetramethyl-chroman-6-yl-)propenyl]-benzoic acid (Compound 34b)

To a solution of 2-trimethylsilanyl-ethyl 4-[3-oxo-3-(2,2,4,4-tetramethyl-chroman-6-yl)-propenyl]-benzoate (Compound 33, 155 mg, 0.33 mmol) in 5 mL of EtOH was added hydroxylamine hydrochloride (46 mg, 0.66 mmol) and pyridine (55 mg, 0.69 mmol). The reaction mixture was then heated at reflux for 6 h. After cooling to room temperature, the solvent was removed in vacuo and the residue was taken up in water. The aqueous layer was adjusted to pH=4-5 with 1 N HCl and extracted with ethyl acetate (3×10 mL). The organic layers were combined and washed with water (2×10 mL) and brine (1×10 mL), dried (MgSO$_4$) and concentrated at reduced pressure. Separation of the E- and Z-isomers was achieved at the ester intermediates by medium pressure liquid chromatography (MPLC) (80:20 hexane/ethyl acetate). Each ester was then dissolved in 2 mL of dimethylsulfoxide (DMSO) and 2 equivalence of tetraethylammomium fluoride (TEAF) was added. After stirring at room temperature for 0.5 h, the mixture was diluted with water (10 mL), extracted with ethyl acetate (3×5 mL), washed with brine (1×5 mL), dried (MgSO$_4$) and concentrated at reduced pressure. Purification by recrystallization with acetonitrile gave Compound 34a (2.2 mg, 2% yield) and Compound 34b (12 mg, 10% yield) as white solids:

$^1$H NMR for Compound 34a (CDCl$_3$, 300 MHz) δ 8.09 (d, J=5.1 Hz, 2H), 8.00 (d, J=1.2 Hz, 2H), 7.76-7.72 (m, 2H), 7.66 (d, J=5.1 Hz, 2H), 7.57 (d, J=9.3 Hz, 1H), 6.80 (d, J=5.1 Hz, 1H), 1.82 (s, 2H), 1.34 (s, 6H), 1.32 (s, 6H);

$^1$H NMR for Compound 34b (CDCl$_3$, 300 MHz) δ 7.97 (d, J=2.4 Hz, 1H), 7.72-7.62 (m, 3H), 7.44 (d, J=8.0 Hz, 1H), 7.47-7.19 (m, 5H), 6.80 (d, J=8.4 Hz, 1H), 1.48 (s, 2H), 1.34 (s, 6H), 1.32 (s, 6H).

Synthesis of Dihydronaphthalene Exemplary Compounds of the Invention

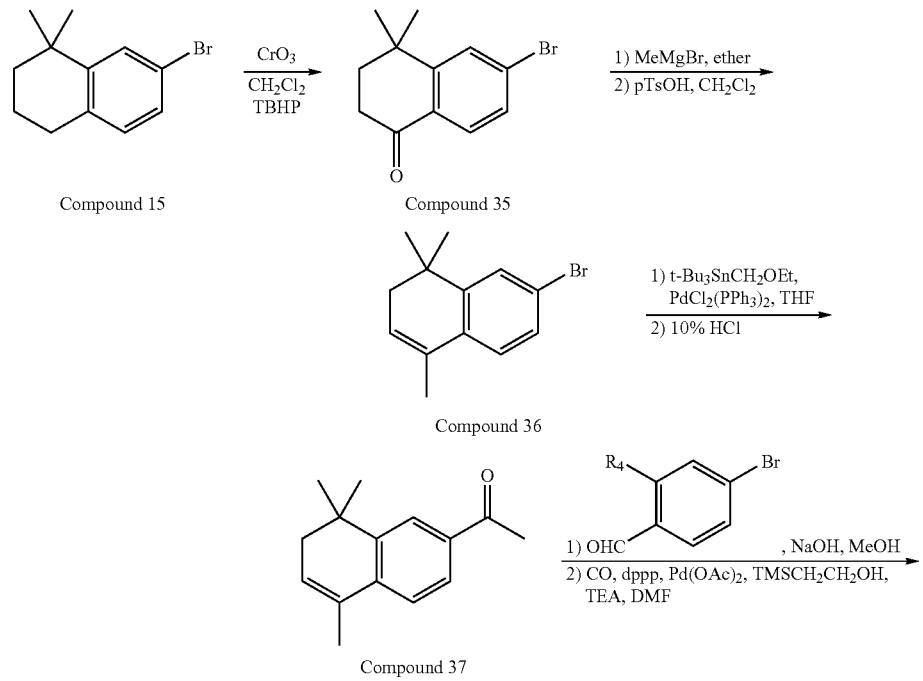

Reaction Scheme 11

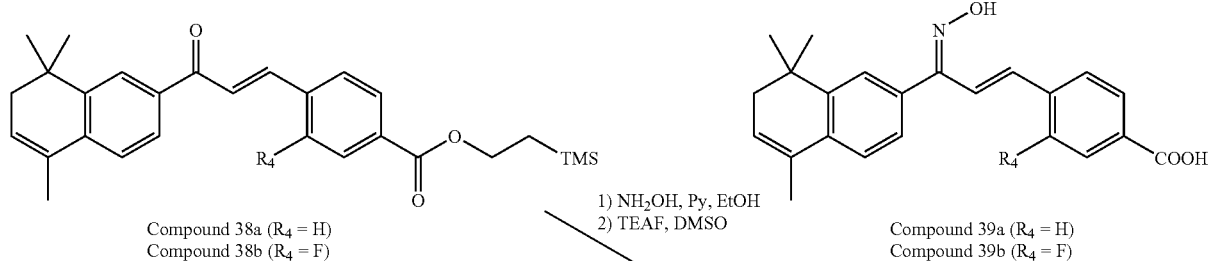

Compound 38a (R₄ = H)
Compound 38b (R₄ = F)

1) NH₂OH, Py, EtOH
2) TEAF, DMSO

Compound 39a (R₄ = H)
Compound 39b (R₄ = F)

+

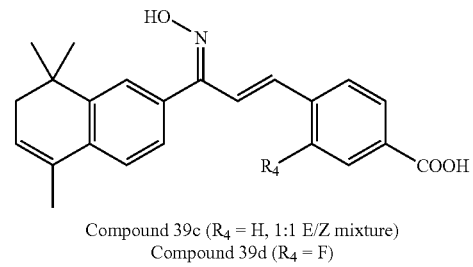

Compound 39c (R₄ = H, 1:1 E/Z mixture)
Compound 39d (R₄ = F)

6-Bromo-4,4-dimethyl-3,4-dihydro-2H-naphthalen-1-one (Compound 35)

To a solution of 7-bromo-1,1-dimethyl-1,2,3,4-tetrahydro-naphthalene (Compound 15, 1.1 g, 4.62 mmol) in 10 mL of dichloromethane was added chromium (VI) oxide (72 mg, 0.46 mmol) and 5 mL of tert-butyl hydroperoxide solution (TBHP). After stirring at room temperature for 8 h, the mixture was diluted with water (20 mL), extracted with diethyl ether (3×10 mL), washed with brine (1×10 mL), dried (MgSO₄) and concentrated at reduced pressure. Purification by flash chromatography (90:10 hexane/ethyl acetate) yielded the title compound (920 mg, 79% yield) as a white solid:

$^1$H NMR (CDCl₃, 300 MHz) δ 7.87 (d, J=8.1 Hz, 1H), 7.54 (d, J=2.1 Hz, 1H), 7.42 (dd, J=2.1, 8.1 Hz, 1H), 2.70 (dd, J=6.3, 7.5 Hz, 2H), 2.01 (dd, J=6.3, 7.5 Hz, 2H), 1.38 (s, 6H).

7-Bromo-1,1,4-trimethyl-1,2-dihydro-naphthalene (Compound 36)

Methyl magnesium bromide (3M solution in diethyl ether, 2.5 mL, 7.50 mmol) was added slowly to a solution of 6-bromo-4,4-dimethyl-3,4-dihydro-2H-naphthalen-1-one (Compound 35, 920 mg, 3.65 mmol) in 10 mL of diethyl ether at 0° C. After stirring and warming to room temperature for 2 h, the mixture was quenched with water at 0° C., extracted with diethyl ether (3×5 mL), washed with brine (1×5 mL), dried (MgSO₄) and concentrated at reduced pressure to give a light yellow oil. The crude oil was then dissolved in 10 mL of dichloromethane and stirred with 100 mg of para-toluene-sulfonic acid at room temperature for 2 h. Water (10 mL) was then added and the organic layer was washed with brine (1×5 mL), dried (MgSO₄) and concentrated at reduced pressure. Purification by flash chromatography (hexane) gave the title compound (589 mg, 65% yield) as a colorless oil:

$^1$H NMR (CDCl₃, 300 MHz) δ 7.40 (d, J=1.8 Hz, 1H), 7.30 (dd, J=1.8, 8.1 Hz, 1H), 7.09 (d, J=8.1 Hz, 1H), 5.77 (t, J=4.5 Hz, 1H), 2.18-2.17 (m, 2H), 2.03 (s, 3H), 1.24 (s, 6H).

1-(5,8,8-Trimethyl-7,8-dihydro-naphthalen-2-yl)-ethanone (Compound 37)

Following General Procedure F and using 7-bromo-1,1,4-trimethyl-1,2-dihydro-naphthalene (Compound 36, 589mg, 2.36 mmol) as the starting material the title compound was obtained (415 mg, 82% yield) as a colorless oil:

$^1$H NMR (CDCl₃, 300 MHz) δ 7.91 (d, J=2.1 Hz, 1H), 7.77 (dd, J=2.1, 8.1 Hz, 1H), 7.31 (d, J=8.1 Hz, 1H), 5.92 (t, J=4.5 Hz, 1H), 2.59 (s, 3H), 2.24-2.22 (m, 2H), 2.09 (s, 3H), 1.29 (s, 6H).

2-Trimethylsilanyl-ethyl 4-[3-oxo-3-(5,8,8-trimethyl-7,8-dihydro-naphthalen-2-yl)-propenyl]-benzoate (Compound 38a)

Following General Procedure D and using 1-(2,2,4,4-tetramethyl-chroman-6-yl)-ethanone (Compound 37, 210 mg, 0.98 mmol) and 4-bromo-benzaldehyde as the starting materials as well as trimethylsilanylethanol instead of ethanol for carboxylation the title compound was obtained (187 mg, 43% yield) as a light yellow oil:

$^1$H NMR (CDCl₃, 300 MHz) δ 8.04 (d, J=7.8 Hz, 2H), 7.88 (d, J=1.8 Hz, 1H), 7.78 (dd, J=1.8, 8.1 Hz, 1H), 7.57 (d, J=7.8 Hz, 2H), 7.49-7.42 (m, 2H), 7.27 (d, J=8.1 Hz, 1H), 5.89-5.82 (m, 1H), 4.37-4.33 (m, 2H), 2.17-2.15 (m, 2H), 2.02 (s, 3H), 1.22 (s, 6H), 1.19-1.08 (m, 2H), 0.00 (s, 9H).

2-Trimethylsilanyl-ethyl 3-fluoro-4-[3-oxo-3-(5,8,8-trimethyl-7,8-dihydro-naphthalen-2-yl)-propenyl]-benzoate (Compound 38b)

Following General Procedure D and using 1-(2,2,4,4-tetramethyl-chroman-6-yl)-ethanone (Compound 37, 206 mg, 0.96 mmol) as the starting materials as well as trimethylsilanylethanol instead of ethanol for carboxylation the title compound was obtained (170 mg, 38% yield) as a light yellow oil:

¹H NMR (CDCl₃, 300 MHz) δ 7.96 (d, J=1.5 Hz, 1H), 7.85-7.66 (m, 6H), 7.33 (d, J=8.1 Hz, 1H), 5.92-5.90 (m, 1H), 4.44-4.41 (m, 2H), 2.25-2.23 (m, 2H) 1.56 (s, 3H), 1.29 (s, 6H), 1.15-1.12 (m, 2H), 0.00 (s, 9H).

E-4-[3-hydroxyimino-3-(5,8,8-trimethyl-7,8-dihydro-naphthalen-2-yl)-propenyl]-benzoic acid (Compound 39a) and 4-[3-hydroxyimino-3-(5,8,8-trimethyl-7,8-dihydro-naphthalen-2-yl)-propenyl]-benzoic acid (Compound 39c)

Following General Procedure G and using 2-trimethylsilanyl-ethyl 4-[3-oxo-3-(5,8,8-trimethyl-7,8-dihydro-naphthalen-2-yl)-propenyl]-benzoate (Compound 38a, 187 mg, 0.42 mmol) as the starting material Compound 39a (17 mg, 11% yield) and Compound 39c (15 mg, 10% yield) were obtained as white solids. Only some E-isomer was isolated from the E/Z mixture of ester intermediates by medium pressure liquid chromatography (MPLC) (90:10 hexane/ethyl acetate) prior to saponification. After saponification each isomer was purified by recrystallization in acetonitrile:

¹H NMR for Compound 39a (CD₃OD, 300 MHz) δ 8.01 (d, J=8.4 Hz, 2H), 7.83 (d, J=16.8 Hz, 1H), 7.67 (d, J=8.4 Hz, 2H), 6.58 (d, J=8.7 Hz, 1H), 7.41-7.28 (m, 2H), 6.80 (d, J=16.8 Hz, 1H), 5.82-5.80 (m, 1H), 2.22-2.20 (m, 2H), 1.97 (s, 3H), 1.25 (s, 6H);

¹H NMR for Compound 39c (1:1 E/Z mixture) (CD₃OD, 300 MHz) δ 8.00-7.93 (m, 2H), 7.83 (d, J=16.8 Hz, 0.5H), 7.58 (d, J=8.1 Hz, 0.5H), 7.49-7.43 (m, 2H), 7.35 (d, J=7.8 Hz, 0.5H), 7.23-7.10 (m, 2.5H), 6.76 (d, J=16.8 Hz, 0.5H), 6.49 (d, J=16.8 Hz, 0.5H), 5.83-5.74 (m, 0.5H), 5.47-5.46 (m, 0.5H), 2.22-2.20 (m, H), 4.14-2.07 (m, 1H), 1.99 (s, 3H), 1.25 (s, 3H), 1.22 (S, 3H).

E-3-fluoro-4-[3-hydroxyimino-3-(5,8,8-trimethyl-7,8-dihydro-naphthalen-2-yl)-propenyl]-benzoic acid (Compound 39b) and Z-3-fluoro4-[3-hydroxyimino-3-(5,8,8-trimethyl-7,8-dihydro-naphthalen-2-yl)-propenyl]-benzoic acid (Compound 39d)

Following General Procedure G and using 2-trimethylsilanyl-ethyl 3-fluoro-4-[3-oxo-3-(5,8,8-trimethyl-7,8-dihydro-naphthalen-2-yl)-propenyl]-benzoate (Compound 38b, 170 mg, 0.37 mmol) as the starting material Compound 39b (31 mg, 22% yield) and Compound 39d (17 mg, 12% yield) were obtained as white solids. Separation of the E- and Z-isomers was achieved at the ester intermediates by medium pressure liquid chromatography (NPLC) (80:20 hexane/ethyl acetate) prior to saponification. After saponification each isomer was purified by recrystallization with acetonitrile:

¹H NMR for Compound 39b (CD₃OD, 300 MHz) δ 7.90 (d, J=7.8 Hz, 1H), 7.75-7.73 (m, 2H), 7.65 (dd, J=1.8, 11.4 Hz, 1H), 7.41 (d, J=1.8 Hz, 1H), 7.31-7.30 (m, 2H), 6.90 (d, J=16.8 Hz, 1H), 5.86-5.82 (m, 1H), 2.16-2.18 (m, 2H), 2.02 (s, 3H), 1.20 (s, 6H);

¹H NMR for Compound 39d (1:1 E/Z mixture) (CD₃OD, 300 MHz) δ 7.91-7.85 (m, 2H), 7.67 (dd, J=1.8, 11.7 Hz, 1H), 7.40-7.30 (m, 3H), 7.22 (dd, J=1.8, 8.1 Hz, 1H), 6.70 (d, J=16.2 Hz, 1H), 5.88-5.84 (m, 1H), 2.26-2.24 (m, 2H), 2.10 (s, 3H), 1.27 (s, 6H).

Synthesis of Indan Exemplary Compounds of the Invention

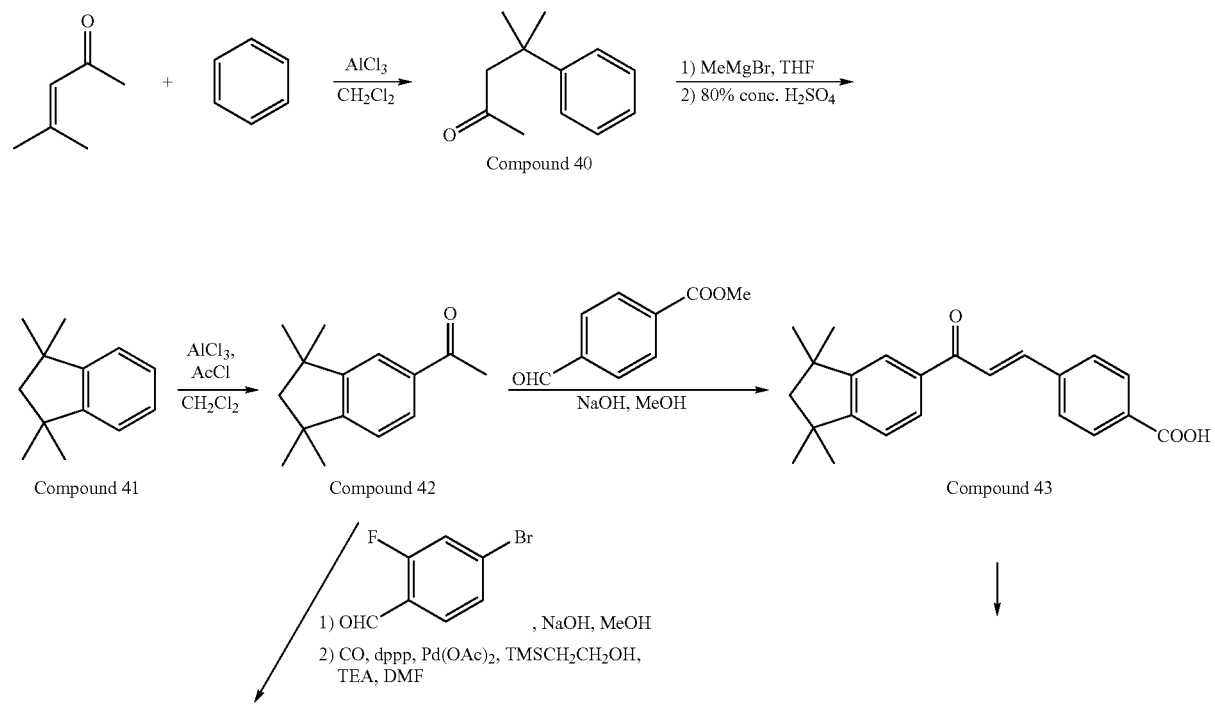

Reaction Scheme 12

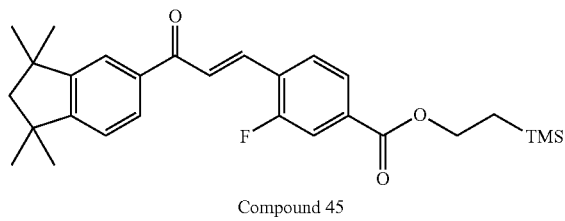

Compound 45

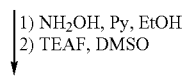
1) NH₂OH, Py, EtOH
2) TEAF, DMSO

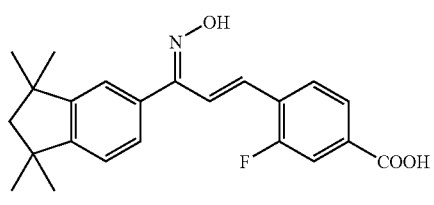

Compound 46a

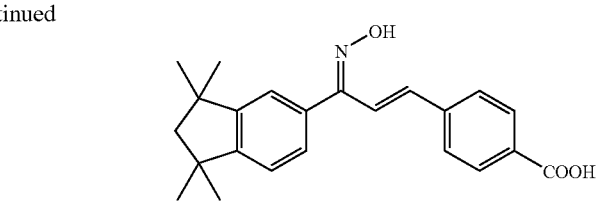

Compound 44a

+

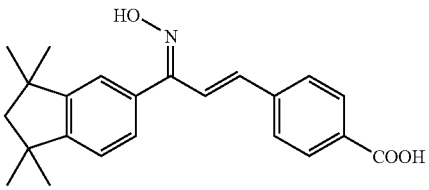

Compound 44b

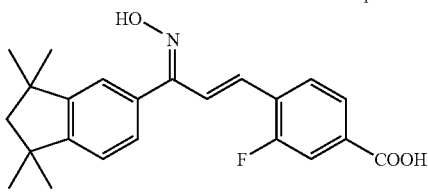

Compound 46b

4-Methyl-4-phenyl-pentan-2-one (Compound 40)

Mesityl oxide (5.9 g, 60.2 mmol) was added drop-wise to a solution of aluminum chloride (10.3 g, 77.4 mmol) in 100 mL of benzene at 0° C. After stirring and warming up to room temperature for 4 h, the mixture was poured to 100 mL of ice-water mixture, extracted with diethyl ether (3×15 mL), and washed with saturated sodium bicarbonate (1×15 mL) and brine (1×15 mL). After the extract was dried (MgSO₄) and concentrated at reduced pressure, high-vacuum distillation of the crude afforded the title compound (7.8 g, 74% yield) as a colorless oil:

$^1$H NMR (CDCl₃, 300 MHz) δ 7.36-7.32 (m, 4H), 7.23-7.18 (m, 1H), 2.74 (s, 2H), 1.80 (s, 3H), 1.43 (s, 6H).

1,1,3,3-Tetramethyl-indan (Compound 41)

Methyl magnesium bromide (3M solution in diethyl ether, 22.2 mL, 66.6 mmol) was added slowly to a solution of 4-methyl-4-phenyl-pentan-2-one (Compound 40, 7.8 g, 44.3 mmol) in 50 mL of tetrahydrofuran (THF) at 0° C. After stirring and warming to room temperature for 2 h, the mixture was quenched with water at 0° C., extracted with ethyl acetate (3×10 mL), washed with brine (1×10 mL), dried (MgSO₄) and concentrated at reduced pressure to give a light yellow oil. The crude oil was then added slowly to 80% concentrated sulfuric acid at 0° C. and the resulting brown mixture was stirred at 0° C. for 1 h. The mixture was then slowly diluted with ice water, extracted with pentane (3×15 mL) and washed with brine (1×15 mL). After the extract was dried (MgSO₄) and concentrated at reduced pressure, high-vacuum distillation of the residue afforded indan the title compound (3.3 g, 43% yield) as a colorless oil:

$^1$H NMR (CDCl₃, 300 MHz) δ 7.12-7.10 (m, 2H), 7.09-7.02 (m, 2H), 1.81 (s, 2H), 1.22 (s, 6H).

1-(1,1,3,3-Tetramethyl-indan-5-yl)-ethanone (Compound 42)

Following General Procedure A and using 1,1,3,3-tetramethyl-indan (Compound 41, 2.3 g, 13.2 mmol) as the starting material the title compound was obtained (2.4 g, 84% yield) as a white solid:

$^1$H NMR (CDCl₃, 300 MHz) δ 7.82 (dd, J=2.1, 8.4 Hz, 1H), 7.76 (d, J=2.1 Hz, 1H), 7.18 (d, J=8.4 Hz, 1H), 2.60 (s, 3H), 1.98 (s, 2H), 1.31 (s, 6H), 1.29 (s, 6H).

4-[3-Oxo-3-(1,1,3,3-tetramethyl-indan-5-yl)-propenyl]-benzoic acid (Compound 43)

Following General Procedure B and using 1-(1,1,3,3-tetramethyl-indan-5-yl)-ethanone (Compound 42, 500 mg, 2.31 mmol) as the starting material the title compound was obtained (738 mg, 92% yield) as a white solid:

$^1$H NMR (CDCl₃, 300 MHz) δ 8.15 (d, J=8.4 Hz, 2H), 7.92-7.86 (m, 2H), 7.82 (d, J=1.8 Hz, 1H), 7.75 (d, J=8.4 Hz, 2H), 7.64 (d, J=15.9 Hz, 1H), 7.26 (d, J=15.9 Hz, 1H), 1.98 (s, 4H), 1.37 (s, 6H), 1.35 (s, 6H).

E-4-[3-Hydroxyimino-3-(1,1,3,3-tetramethyl-indan-5-yl)-propenyl]-benzoic acid (Compound 44a) and
Z-4-[3-hydroxyimino-3-(1,1,3,3-tetramethyl-indan-5-yl)-propenyl]-benzoic acid (Compound 44b)

Following General Procedure C and using 4-[3-oxo-3-(1,1,3,3-tetramethyl-indan-5-yl)-propenyl]-benzoic acid (Compound 43, 210 mg, 0.55 mmol) as the starting material Compound 44a (59 mg, 30% yield) and Compound 44b (18 mg, 9% yield) were obtained as white solids:

¹H NMR for Compound 44a (acetone-d₆, 300 MHz) δ 8.04 (d, J=8.1 Hz, 2H), 7.85 (d, J=16.8 Hz, 1H), 7.70 (d, J=8.1 Hz, 2H), 7.37-7.11 (m, 3H), 6.90 (d, J=16.8 Hz, 1H), 1.97 (s, 2H), 1.34 (s, 6H), 1.33 (s, 6H);

¹H NMR for Compound 44b (acetone-d₆, 300 MHz) δ 8.00 (d, J=6.0 Hz, 2H), 7.60 (d, J=6.0 Hz, 1H), 7.27-7.15 (m, 4H), 6.56 (d, J=15.0 Hz, 1H), 1.99 (s, 2H), 1.36 (s, 6H), 1.35 (s, 6H).

¹H NMR for Compound 46a (acetone-d₆, 300 MHz) δ 7.96-7.90 (m, 3H), 7.71 (d, J=11.7 Hz, 1H), 7.38-7.32 (m, 2H), 7.23 (d, J=6.9 Hz, 1H), 7.02 (d, J=16.8 Hz, 1H), 1.97 (s, 2H), 1.34 (s, 6H), 1.33 (s, 6H);

¹H NMR for Compound 46b (acetone-i, 300 MHz) δ 7.84-7.65 (m, 3H), 7.35-7.16 (m, 4H), 6.69 (d, J=16.8 Hz, 1H), 1.98 (s, 2H), 1.34 (s, 6H), 1.33 (s, 6H).

Synthesis of Quinoxaline Exemplary Compounds of the Invention

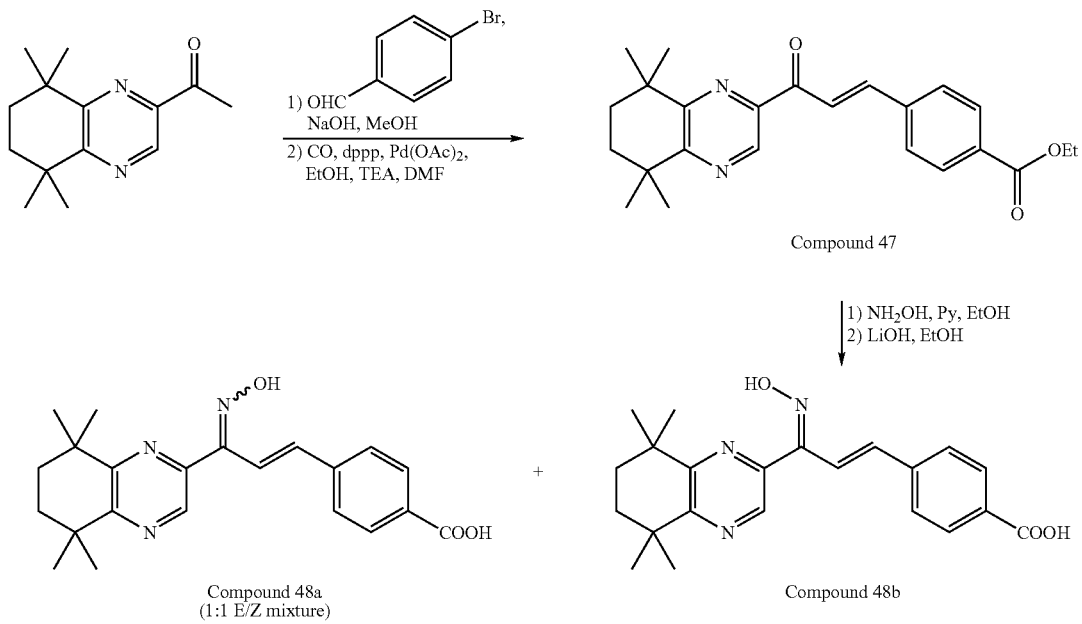

Reaction Scheme 13

2-Trimethylsilanyl-ethyl 3-fluoro-4-[3-oxo-3-(1,1,3,3-tetramethyl-indan-5-yl)-propenyl]-benzoate (Compound 45)

Following General Procedure D and using 1-(1,1,3,3-tetramethyl-indan-5-yl)-ethanone (Compound 42, 500 mg, 2.31 mmol) as the starting materials as well as trimethylsilanylethanol instead of ethanol for carboxylation the title compound (95 mg, 9% yield) was obtained as a yellow oil:

¹H NMR (CDCl₃, 300 MHz) δ 7.83-7.62 (m, 7H), 7.18 (d, J=9.6 Hz, 1H), 4.41-4.37 (m, 2H), 1.91 (s, 2H), 1.30 (s, 6H), 1.28 (s, 6H), 1.09-1.06 (m, 2H), 0.00 (s, 9H).

E-3-fluoro-4-[3-hydroxyimino-3-(1,1,3,3-tetramethyl-indan-5-yl)-propenyl]-benzoic acid (Compound 46a) and Z-3-fluoro-4-[3-hydroxyimino-3-(1,1,3,3-tetramethyl-indan-5-yl)-propenyl]-benzoic acid (Compound 46b)

Following General Procedure G while using 2-trimethylsilanyl-ethyl 3-fluoro-4-[3-oxo-3-(1,1,3,3-tetramethyl-indan-5-yl)-propenyl]-benzoate (Compound 45, 95 mg, 0.20 mmol) as the starting material Compound 46a (28 mg, 36% yield) and Compound 46b (12 mg, 15% yield) were obtained as white solids:

Ethyl 4-[3-oxo-3-(5,5,8,8-tetramethyl-5,6,7,8-tetrahydro-quinoxalin-2-yl)-propenyl]-benzoate (Compound 47)

Following General Procedure D and using 1-(5,5,8,8-tetramethyl-5,6,7,8-tetrahydro-quinoxalin-2-yl)-ethanone (prepared according to the procedures published in Journal of Medicinal Chemistry 2000, 43, 409-19, expressly incorporated herein by reference) (232 mg, 1.00 mmol) as the starting material afforded the title compound (123 mg, 31% yield) as a light yellow solid:

¹H NMR (CDCl₃, 300 MHz) δ 9.04 (s, 1H), 8.18 (d, J=16.2 Hz, 2H), 8.03 (d, J=8.1 Hz, 2H), 7.88 (d, J=16.2 Hz, 1H), 7.66 (d, J=8.1 Hz, 2H), 4.34 (q, J=7.2 Hz, 2H), 1.79 (s, 4H), 1.35 (s, 6H), 1.29 (s, 6H), 1.26 (t, J=7.2 Hz, 3H).

4-[3-Hydroxyimino-3-(5,5,8,8-tetramethyl-5,6,7,8-tetrahydro-quinoxalin-2-yl)-propenyl]-benzoic acid (Compound 48a) and Z-4-[3-hydroxyimino-3-(5,5,8,8-tetramethyl-5,6,7,8-tetrahydro-quinoxalin-2-yl)-propenyl]-benzoic acid (Compound 48b)

Following General Procedure E and using ethyl 4-[3-oxo-3-(5,5,8,8-tetramethyl-5,6,7,8-tetrahydro-quinoxalin-2-yl)-propenyl]-benzoate (Compound 47, 123 mg, 0.31 mmol) as the starting material Compound 48a (10 mg, 8% yield) and Compound 46b (12 mg, 10% yield) were obtained as white solids:

¹H NMR for Compound 48a (acetone-4, 300 MHz) δ 8.57 (s, 0.5H), 8.55 (s, 0.5H), 8.00-7.87 (m, 2H), 7.73-7.47 (m, 3H), 7.14 (d, J=16.5 Hz, 0.5H), 6.69 (d, J=16.8 Hz, 0.5H), 1.76 (s, 2H), 1.75 (s, 2H), 1.26 (s, 6H), 1.22 (s, 6H);

¹H NMR for Compound 48b (acetone-d₆, 300 MHz) δ 8.55 (s, 1H), 7.87 (d, J=8.4 Hz, 2H), 7.48 (d, J=8.4 Hz, 2H), 7.15 (d, J=16.5 Hz, 1H), 6.68 (d, J=16.5 Hz, 1H), 1.76 (s, 4H), 1.25 (s, 12H).

Synthesis of Thiochromene, Chromene, Benzofuran and Isobenzofuran Compounds of the Invention Reaction Scheme 14 serves as an example for preparing compounds of the invention which are benzodihydrofuran derivatives, that is where the variable R of Formula 1 is represented by Formula (c) or Formula (d). More specifically, Reaction Scheme 14 and the following reaction schemes illustrate the synthesis of bromo compounds within the scope of Formula 10 from which compounds of the invention can be obtained by the steps shown in Reaction Scheme 3b.

For the sake of simplicity Reaction Scheme 14 illustrates the synthesis of the compounds of the invention where the variable (RI)m represents geminal dimethyl groups substituting one or two carbons of the non-aromatic portion of the dihydrobenzofuran nucleus. Thus, in accordance with this scheme phthalic acid diethylester (available from Aldrich) is reacted methylmagnesium bromide and thereafter with acid to provide 2,2,7,7-tetramethyl-dihydro-iso-benzofuran of Formula 11. The dihydro-iso-benzofuran of Formula 11 is then reacted with N-bromosuccinimide (NBS) in tetrahydrofuran (THF) to give 4-bromo-2,2,7,7-tetramethyl-dihydro-iso-benzofuran of Formula 12.

In another exemplary sequence of reactions, 4-bromophenol is reacted with 3-chloro-2-methyl-prop-1-ene in the presence of strong acid (H₂SO₄), and thereafter with strong base (NaH) to provide 3,3-dimethyl-5-bromo-dihydrobenzofuran of Formula 13. The bromo compounds of Formulas 12 and 13 are subjected to the same sequence of reactions (not shown in Scheme 14) as the bromo compounds of Formula 10 in Reaction Scheme 3 to provide compounds of the invention in accordance with Formula 1 where the variable R is dihydro-iso-benzofuran or dihydrobenzofuran radical.

Reaction Scheme 14

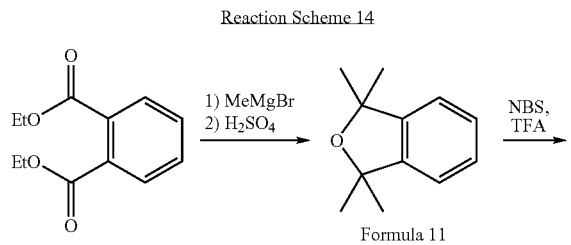

Formula 11

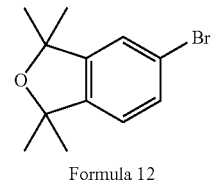

Formula 12

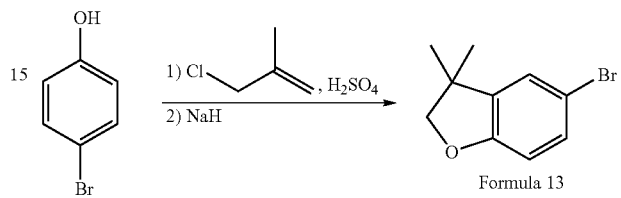

Formula 13

Reaction Scheme 15 provides examples for preparing compounds of the invention which are chromene or thiochromene derivatives, that is where the variable R of Formula 1 is represented by Formula (f) and where the dashed line represents presence of a bond. For the sake of simplicity of illustration the scheme illustrates the synthesis of the compounds of the invention where the variable (R₁)ₘ represents geminal dimethyl groups substituting carbon 2 of the non-aromatic portion of the chromene or thiochromene nucleus. Thus, in accordance with this scheme, 4-bromophenol or 4-bromothiophenol is reacted with dimethylacryloyl chloride to provide the corresponding ester or thioester of Formula 14. The ester or thioester of Formula 14 is then cyclized under Friedel Crafts conditions to provide the 7-bromo-thiochroman-4-one or the 7-bromo-chroman-4-one of Formula 15. The compound of Formula 15 is reacted with a Grignard reagent of the formula R₁MgX (where X is halogen and R₁ is defined as in connection with Formula 1) and then with acid to provide the 7-bromo-2,2-dimethyl-thio-chromene or corresponding chromene derivative of Formula 16.

In another exemplary reaction sequence shown in Reaction Scheme 15, 4-bromophenol is reacted with acetyl chloride (AcCl) to provide the corresponding ester, and the ester made to undergo a Fries rearrangement under Friedel Crafts conditions to provide 2-acetyl-4-bromophenol. 2-Acetyl-4-bromophenol is reacted with acetone in the presence of piperidine and trifluoroacetic acid (TFA) to give 6-bromo-2,2-dimethyl-chroman-4-one. The latter compound is reacted with the Grignard reagent of the formula R₁MgX and then with acid to provide the 6-bromo-2,2-dimethyl-chromene derivative of Formula 17.

In still another exemplary reaction sequence shown in Reaction Scheme 15 4-bromo-thiophenol is reacted with 2,2-dimethylacryloic acid in the presence of piperidine to provide an adduct of Formula 18 that is cyclized by treatment with methanesulfonic acid to give 6-bromo-2,2-dimethyl-thiochroman-4-one of Formula 19. The compound of Formula 19 is reacted with the Grignard reagent of the formula R₁MgX and then with acid to provide the 6-bromo-2,2-dimethyl-thiochromene derivative of Formula 20.

The bromo compounds of Formulas 16, 17 and 20 are subjected to the same sequence of reactions (not shown in Scheme 15) as the bromo compounds of Formula 10 of Reaction Scheme 3 to provide compounds of the invention in accordance with Formula 1 where the variable R is a chromene or a thiochromene radical.

Reaction Scheme 15
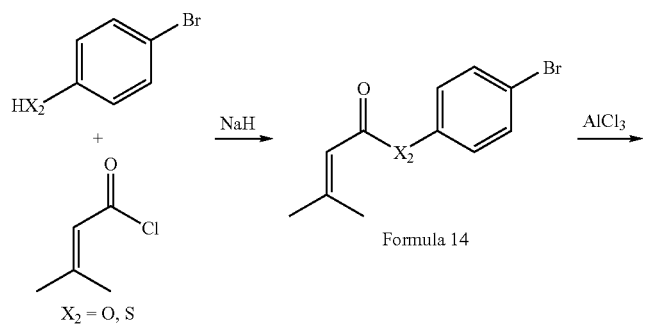
Formula 14
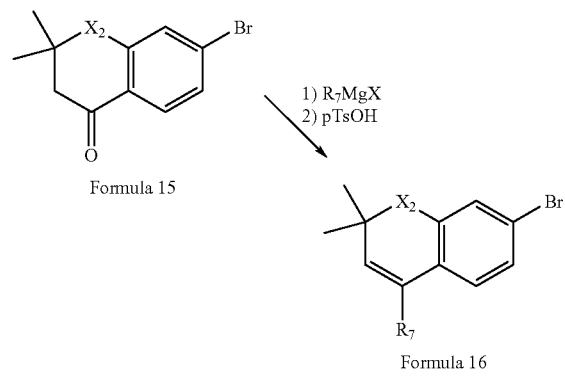
Formula 15
Formula 16
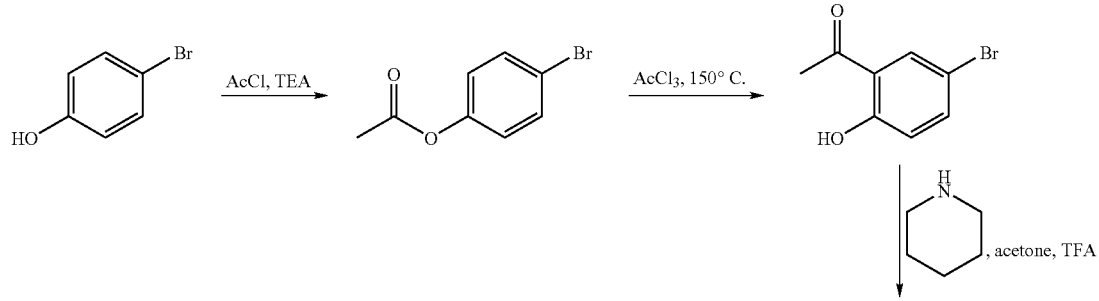
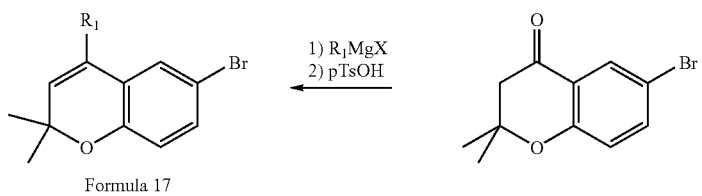
Formula 17
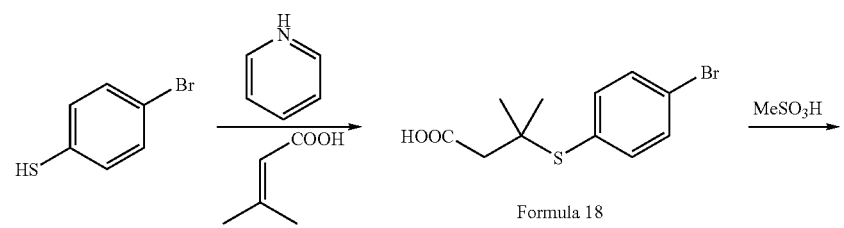
Formula 18

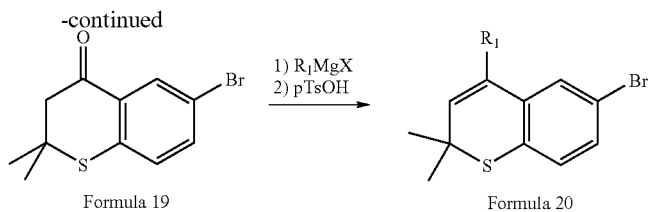

Formula 19 → Formula 20

What is claimed is:

1. A compound of the formula

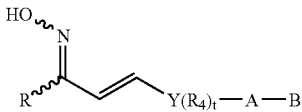

wherein R is selected from the groups consisting of the radicals defined by formulas (a) through (g)

Formula (a)
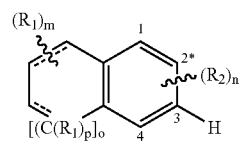

Formula (b)
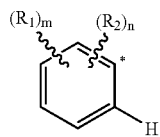

Formula (c)
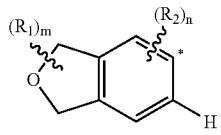

Formula (d)
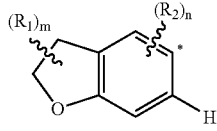

Formula (e)
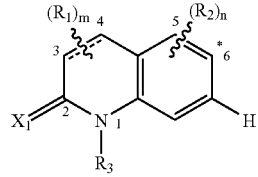

Formula (f)
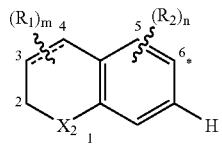

Formula (g)
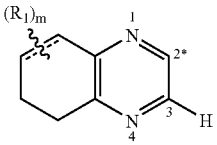

where the dashed line in a ring represents a bond, or absence of a bond with the proviso that only one of the two dashed lines in the ring can represent a bond;

a * denotes a ring carbon to which the chalcone oxime group is attached;

$X_1$ is O or S attached to the adjacent carbon with a double bond, or $X_1$ represents two $R_1$ groups attached to the adjacent carbon;

$X_2$ is O or S;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl;

t is 0, 1 or 2;

m is an integer having the values 0 to 6;

n is an integer having the values 0 to 2;

o is an integer having the values 0 or 1;

p is an integer having the values 1 or 2;

$R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_3$ is H or alkyl of 1 to 10 carbons;

$R_4$ is independently halogen, alkyl of 1 to 10 carbons, fluoro substituted alkyl of 1 to 6 carbons, alkoxy of 1 to 10 carbons, or alkylthio of 1 to 10 carbons;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

2. A compound of the formula

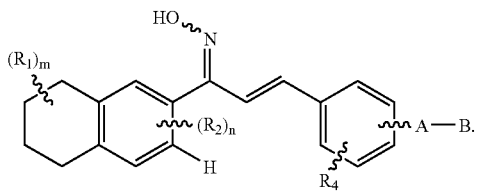

where $R_1$ is independently alkyl of 1 to 6 carbons, $COOR_3$, F, Cl, Br or I;
$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
$R_3$ is H or alkyl of 1 to 10 carbons;
$R_4$ is H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 8;
n is an integer having the values 0 to 2;
A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

3. A compound in accordance with claim 2 that has the formula

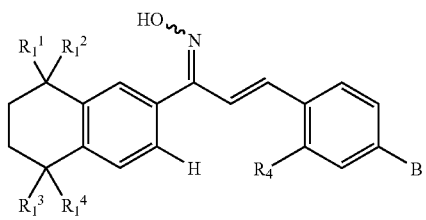

where $R_1^1$, $R_1^2$, $R_1^3$ and $R_1^4$ independently are hydrogen or methyl;
$R_4$ is hydrogen or F, and
B is COH or $COOR_8$ or a pharmaceutically acceptable salt of said compound.

4. A compound in accordance with claim 3 that has the formula

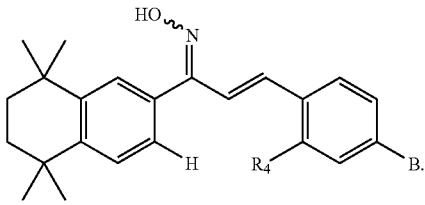

5. A compound in accordance with claim 4 where $R_4$ is H.
6. A compound in accordance with claim 4 where $R_4$ is F.
7. A compound in accordance with claim 3 that has the formula

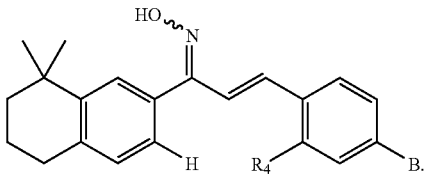

8. A compound in accordance with claim 7 where $R_4$ is H.
9. A compound in accordance with claim 7 where $R_4$ is F.
10. A compound in accordance with claim 3 that has the formula

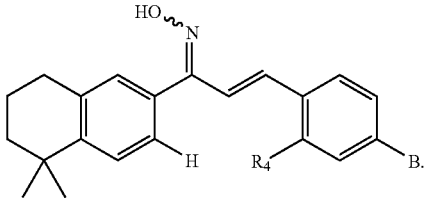

11. A compound in accordance with claim 10 where $R_4$ is H.
12. A compound of the formula

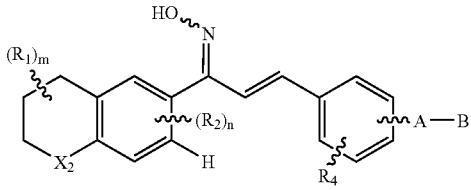

where $X_2$ is O or S;
$R_1$ is independently alkyl of 1 to 6 carbons, $COOR_3$, F, Cl, Br or I;
$R_2$ is independently alkyl of 1 to 6-carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
$R_3$ is H or alkyl of 1 to 10 carbons;
$R_4$ is independently H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

13. A compound of the formula

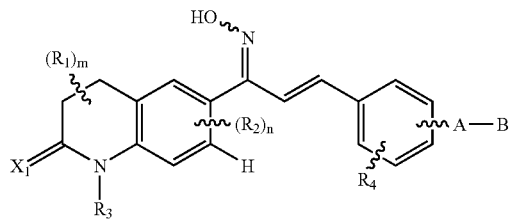

where $X_1$ is O or S attached to the adjacent carbon with a double bond, or $X_1$ represents two $R_1$ groups attached to the adjacent carbon;

$R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 4;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CQNR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

14. A compound in accordance with claim 13 that has the formula

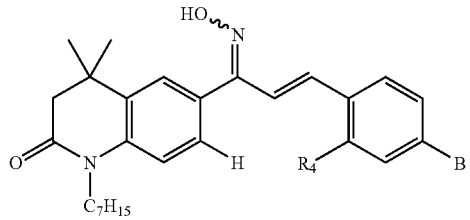

where $R_4$ is hydrogen or F, and

B is COOH or $COOR_8$ or a pharmaceutically acceptable salt of said compound.

15. A compound in accordance with claim 14 where $R_4$ is H.

16. A compound of the formula

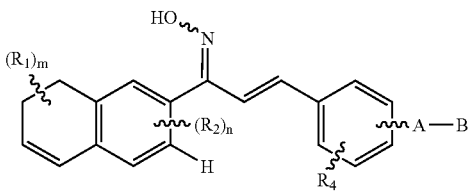

where $R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

17. A compound of the formula

[Chemical structure: indane fused ring with HO–N= substituent, $(R_1)_m$, $(R_2)_n$, H, connected via C=C to phenyl group bearing $R_4$ and A—B]

where
- $R_1$ is independently alkyl of 1 to 6 carbons, $COOR_3$, F, Cl, Br or I;
- $R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
- $R_3$ is H or alkyl of 1 to 10 carbons;
- $R_4$ is H, halogen, alkyl of 1 to 10 carbons, fluoro substituted alkyl of 1 to 6 carbons, alkoxy of 1 to 10 carbons, or alkylthio of 1 to 10 carbons;
- m is an integer having the values 0 to 6;
- n is an integer having the values 0 to 2;
- A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
- B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

18. A compound of the formula

[Chemical structure: tetrahydroquinoxaline fused ring with HO–N= substituent, $(R_1)_m$, H, connected via C=C to phenyl group bearing $R_4$ and A—B]

where
- $R_1$ is independently alkyl of 1 to 6 carbons, $COOR_3$, F, Cl, Br or I;
- $R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
- $R_3$ is H or alkyl of 1 to 10 carbons;
- $R_4$ is H, halogen, alkyl of 1 to 10 carbons, fluoro substituted alkyl of 1 to 6 carbons, alkoxy of 1 to 10 carbons, or alkylthio of 1 to 10 carbons;
- m is an integer having the values 0 to 8;
- A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
- B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the allyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

19. A compound in accordance with claim 5 that has the formula

[Chemical structure: tetramethyl-tetrahydronaphthalene with N–OH group, connected via trans-CH=CH to phenyl-COOH]

or a pharmaceutically acceptable salt of said compound.

20. A compound in accordance with claim 6 that has the formula

[Chemical structure: tetramethyl-tetrahydronaphthalene with N–OH group, connected via trans-CH=CH to fluoro-phenyl-COOH]

or a pharmaceutically acceptable salt of said compound.

21. A compound in accordance with claim 8 that has the formula

[Chemical structure: dimethyl-tetrahydronaphthalene with N–OH group, connected via trans-CH=CH to phenyl-COOH]

or a pharmaceutically acceptable salt of said compound.

22. A compound in accordance with claim 12 that has the formula

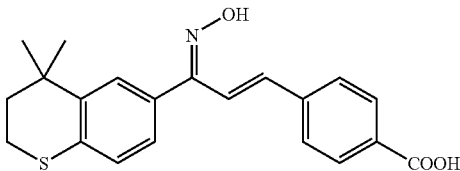

or a pharmaceutically acceptable salt of said compound.

23. A compound in accordance with claim 16 that has the formula

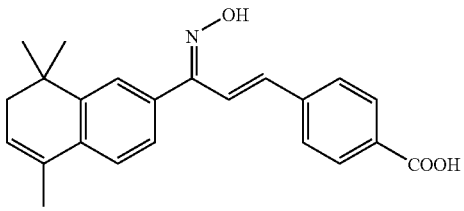

or a pharmaceutically acceptable salt of said compound.

24. A compound in accordance with claim 17 that has the formula

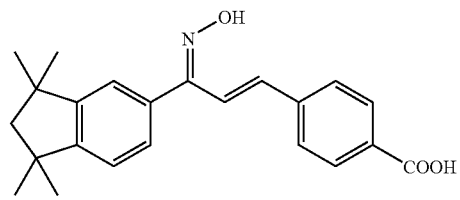

or a pharmaceutically acceptable salt of said compound.

25. A process of treating emphysema or a related pulmonary insufficiency condition administering to a mammal in need of such treatment a compound in accordance with claim 1.

26. A process in accordance with claim 25 wherein the compound is of the formula:

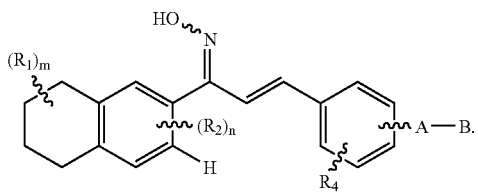

where
$R_1$ is independently alkyl of 1 to 6 carbons, $COOR_3$, F, Cl, Br or I;
$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
$R_3$ is H or alkyl of 1 to 10carbons;
$R_4$ is H, halogen, alkyl of 1 to 10 carbons, fluoro substituted alkyl of 1 to 6 carbons, alkoxy of 1 to 10 carbons;
m is an integer having the values 0 to 8;
n is an integer having the values 0 to 2;
A is $(CH_2)_q$ where q is 0-5, lower branched chain alkyl having 3-6 carbons, cycloalkyl having 3-6 carbons. alkenyl having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$alkylphenyl, $R_9$ and $R_{10}$ independently are hydrogen, an alkyl group of 1 to 10 carbons, or a cycloalkyl group of 5-10 carbons, or phenyl $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

27. A process in accordance with claim 25 wherein the compound is of the formula:

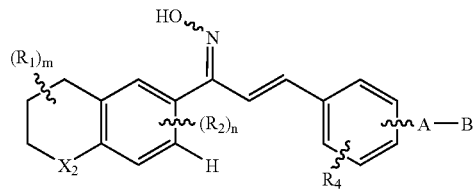

where
$X_2$ O or S;
$R_1$ is independently alkyl of 1 to 6 carbons, $COOR_3$, F, Cl, Br or I;
$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
$R_3$ is H or alkyl of 1 to 10 carbons;
$R_4$ is independently H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 6;
n is an integer having the values 0 to 2;
A is $(CH_2)_q$ where q is 0-5, lower branched chain alkyl having 3-6 carbons, cycloalkyl having 3-6 carbons, alkenyi having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$alkylphenyl, $R_9$ and $R_{10}$ independently are hydrogen, an alkyl group of 1 to 10 carbons, or a cycloalkyl group of 5-10 carbons, or phenyl or $C_{1-6}$alkyiphenyl, $R_{11}$ is alkyl of 1 to 6carbons,phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

28. A process in accordance with claim 25 wherein the compound is of the formula:

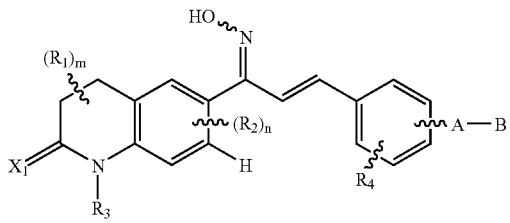

where $X_1$ is O or S attached to the adjacent carbon with a double bond, or $X_1$ represents two $R_1$ groups attached to the adjacent carbon;

$R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2, C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 4;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof $COOR_8$, $CON_9R_{10}$, —$CH_2CH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkenyl where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

29. A process in accordance with claim 25 wherein the compound is of the formula:

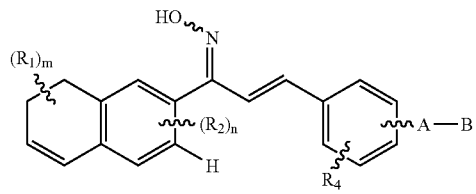

where $R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2, C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$ $(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6carbons, phenyl or $C_{1-6}$alkylphenyl, $R_{12}$ is alkyl of 1 to 6 carbons, and R13 is divalent alkyl radical of 2-5 carbons, or a pharmaceutically acceptable salt of said compound.

30. A process in accordance with claim 25 wherein the compound is of the formula:

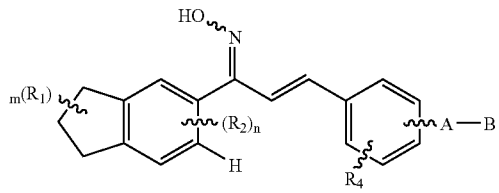

where $R_1$ is independently alkyl of 1 to 6 carbons, $COOR_3$,F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2, C_{1-6}$alkylamino or di ($C_{1-6}$alkyl)amino;

$R_3$ is H or alkyl of 1 to 10 carbons;

$R_4$ is independently H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;

n is an integer having the values 0 to 2;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2, CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilvialkyl where the alkyl group has 1 to 10 carbons, or a cycloalkyl group of 5 to 10 carbons, CH₂OCH₃ or CH₂OCH₂OOC₁₋₆alkyl, or R₈ is phenyl or C₁₋₆alkyiphenyl, R₉ and R₁₀ independently are hydrogen, an alkyl group of 1 to 10 carbons, or a cycloalkyl group of 5-10 carbons, or phenyl or C₁₋₆alkylphenyl, R₁₁ is alkyl of 1 to 6 carbons, phenyl or C₁₋₆alkylphenyl, R₁₂ is alkyl of 1 to 6 carbons, and R₁₃ is divalent alkyl radical of 2-5 carbons, or a pharmaceutically acceptable salt of said compound.

31. A process in accordance with claim 25 wherein the of the formula:

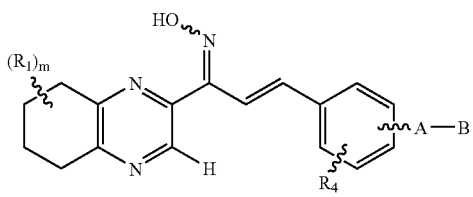

where
R₁ is independently alkyl of 1 to 6 carbons, COOR₃, F, Cl, Br or I;
R₂ is independently alkyl of 1 to 6 carbons, F, Cl, Br, I, OH, SH, alkoxy having 1 to 6 carbons, alkylthio having 1 to 6 carbons, NH₂C₁₋₆alkylamino or di(C₁₋₆alkyl)amino;
R₃ is H or alkyl of 1 to 110 carbons;
R₄ is H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 8;
A is (CH₂)q where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, COOR₈, CONR₉R₁₀, —CH₂OH, CH₂OR₁₁, CH₂OCOR₁₁, CHO, CH(OR₁₂)₂, CHOR₁₃O, —COR₇, CR₇(OR₁₂)₂, CR₇OR₁₃O, or tri-lower alkylsilyl, where R₇ is an alkyl group of 1 to 6 carbons, cycloalkyl of 3 to 5 carbons, or cycloalkyl of 3 to 5 carbons, or alkenyl group containing 2 to 5 carbons, R₈ is an alkyl group of 1 to 10 carbons or trimethylsilylalkyl where the alkyl group has 1 to 10 carbons, or a cycloalkyl group of 5 to 10 carbons, CH₂OCH₃ or CH₂OCH₂OOC₁₋₆alkyl, or R₈ is phenyl or C₁₋₆ alkyiphenyl, R₉ and R₁₀ independently are hydrogen, an alkyl group of 1 to 10 carbons, or a cycloalkyl group of 5-10 carbons, or phenyl or C₁₋₆alkylphenyl, R₁₁ is alkyl of 1 to 6 carbons, phenyl or C₁₋₆alkylphenyl, R₁₂ is alkyl of 1 to 6 carbons, and R₁₃ is divalent alkyl radical of 2-5 carbons, or a pharmaceutically acceptable salt of said compound.

32. A process of treating a disease or condition that is responsive to RARγ agonist retinoids, comprising administering to a mammal in need thereof, a compound in accordance with claim 1, wherein the disease or condition that is responsive to RARγ agonist retinoids is selected from the group consisting of acne and psoriasis.

33. A process in accordance with claim 32, wherein the compound is represented by the formula:

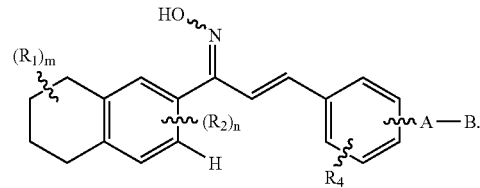

where
R₁ is independently alkyl of 1 to 6 carbons, COOR3, F, Cl, Br or I;
R₂ is independently alkyl of 1 to 6 carbons, F, Cl, Br, I, OH, SH, alkoxy having 1 to 6 carbons, alkylthio having 1 to 6 carbons, NH₂, C₁₋₆alkylamino or di(C₁₋₆alkyl)amino;
R₃ is H or alkyl of 1 to 10 carbons;
R₄ is H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 8;
n is an integer having the values 0 to 2;
A is (CH₂)q where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, COOR₈, CONR₉R₁₀, —CH₂OH, CH₂OR₁₁, CH₂OCOR₁₁, CHO, CH(OR₁₂)₂, CHOR₁₃O, —COR₇, CR7(OR₁₂)₂, CR₇OR₁₃O, or tri-lower alkylsilyl, where R₇ is an alkyl group of 1 to 6 carbons, cycloalkyl of 3 to 5 carbons, or alkenyl group containing 2 to 5 carbons, R₈ is an alkyl group of 1 to 10 carbons or trimethylsilylalkyl where the alkyl group has 1 to 10 carbons, or a cycloalkyl group of 5 to 10 carbons, CH₂OCH₃ or CH₂OCH₂OOC₁₋₆alkyl, or R₈ is phenyl or C₁₋₆ alkylphenyl, R₉ and R₁₀ independently are hydrogen, an alkyl group of 1 to 10 carbons, or a cycloalkyl group of 5-10 carbons, or phenyl or C₁₋₆alkylphenyl, R₁₁ is alkyl of 1 to 6 carbons, phenyl or C₁₋₆alkylphenyl, R₁₂ is alkyl of 1 to 6 carbons, and R₁₃ is divalent alkyl radical of 2-5 carbons, or a pharmaceutically acceptable salt of said compound.

34. A process in accordance with claim 32, wherein the compound is represented by the formula:

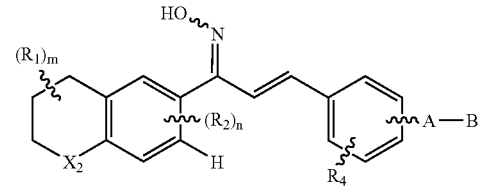

where
X₂ is O or S;
R₁ is independently alkyl of 1 to 6 carbons, COOR₃, F, Cl, Br or I;
R₂ is independently alkyl of 1 to 6 carbons, F, Cl, Br, I, OH, SH, alkoxy having 1 to 6 carbons, alkylthio having 1 to 6 carbons, NH₂, C₁₋₆alkylamino or di(C₁₋₆alkyl)amino;
R₃ is H or alkyl of 1 to 10 carbons;
R₄ is independently H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;
n is an integer having the values 0 to 2;
A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkyiphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

35. A process in accordance with claim 32, wherein the compound is represented by the formula:

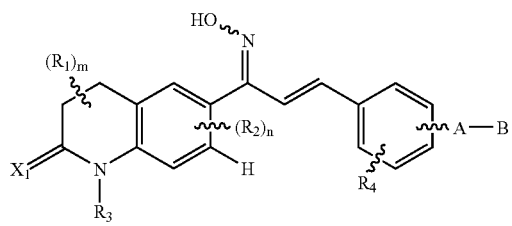

where $X_1$ is O or S attached to the adjacent carbon with a double bond, or $X_1$ represents two $R_1$ groups attached to the adjacent carbon;

$R_1$ is independently alkyl of 1 to 6 carbons, COOR3, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 4;
n is an integer having the values 0 to 2;
A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkyiphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

36. A process in accordance with claim 32, wherein the compound is represented by the formula:

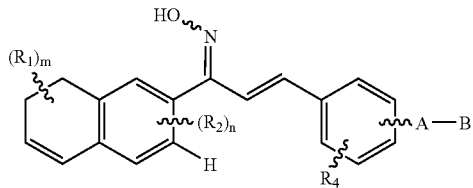

where $R_1$ is independently alkyl of 1 to 6 carbons, $COOR_3$, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_3$ is H or alkyl of 1 to 10 carbons;

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values 0 to 6;
n is an integer having the values 0 to 2;
A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkyiphenyl, $R_9$ and $R_{10}$ independently are hydrogen, an alkyl group of 1 to 10 carbons, or a cycloalkyl group of 5-10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2-5 carbons, or a pharmaceutically acceptable salt of said compound.

37. A process in accordance with claim 32, wherein the compound is represented by the formula:

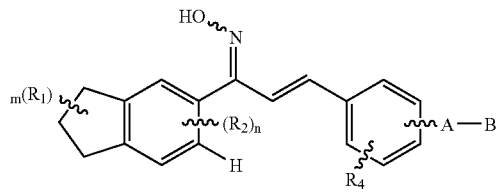

where
R₁ is independently alkyl of 1 to 6 carbons, COOR₃, F, Cl, Br or I;
R₂ is independently alkyl of 1 to 6 carbons, F, Cl, Br, I, OH, SH, alkoxy having 1 to 6 carbons, alkylthio having 1 to 6 carbons, NH₂, C₁₋₆alkylamino or di(C₁₋₆alkyl)amino;
R₃ is H or alkyl of 1 to 10 carbons;
R₄ is independently H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 6;
n is an integer having the values 0 to 2;
A is (CH₂)_q where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, COOR₈, CONR₉R₁₀, —CH₂OH, CH₂OR₁₁, CH₂OCOR₁₁, CHO, CH(OR₁₂)₂, CHOR₁₃O, —COR₇, CR₇(OR₁₂)₂, CR₇OR₁₃O, or tri-lower alkylsilyl, where R₇ is an alkyl group of 1 to 6 carbons, cycloalkyl of 3 to 5 carbons, or alkenyl group containing 2 to 5 carbons, R₈ is an alkyl group of 1 to 10 carbons or trimethylsilylalkyl where the alkyl group has 1 to 10 carbons, or a cycloalkyl group of 5 to 10 carbons, CH₂OCH₃ or CH₂OCH₂OOC₁₋₆alkyl, or R₈ is phenyl or C₁₋₆ alkylphenyl, R₉ and R₁₀ independently are hydrogen, an alkyl group of 1 to 10 carbons, or a cycloalkyl group of 5-10 carbons, or phenyl or C₁₋₆alkylphenyl, R₁₁ is alkyl of 1 to 6 carbons, phenyl or C₁₋₆alkylphenyl, R₁₂ is alkyl of 1 to 6 carbons, and R13 is divalent alkyl radical of 2-5 carbons, or a pharmaceutically acceptable salt of said compound.

38. A process in accordance with claim 32, wherein the compound is represented by the formula:

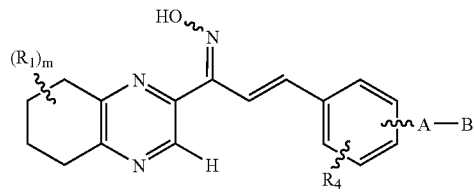

where
R₁ is independently alkyl of 1 to 6 carbons, COOR₃, F, Cl, Br or I;
R₂ is independently alkyl of 1 to 6 carbons, F, Cl, Br, I, OH, SH, alkoxy having 1 to 6 carbons, alkylthio having 1 to 6 carbons, NH₂, C₁₋₆alkylamino or di(C₁₋₆alkyl)amino;
R₃ is H or alkyl of 1 to 10 carbons;
R₄ is H, halogen, alkyl of 1 to 10 carbons, fluoro substituted alkyl of 1 to 6 carbons, alkoxy of 1 to 10 carbons, or alkylthio of 1 to 10 carbons;
m is an integer having the values 0 to 8;
A is (CH₂)_q where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;
B is COOH or a pharmaceutically acceptable salt thereof, COOR₈, CONR₉R₁₀, —CH₂OH, CH₂OR₁₁, CH₂OCOR₁₁, CHO, CH(OR₁₂)₂, CHOR₁₃O, —COR₇, CR₇(OR₁₂)₂, CR₇OR₁₃O, or tri-lower alkylsilyl, where R₇ is an alkyl group of 1 to 6 carbons, cycloalkyl of 3 to 5 carbons, or alkenyl group containing 2 to 5 carbons, R₈ is an alkyl group of 1 to 10 carbons or trimethylsilylalkyl where the alkyl group has 1 to 10 carbons, or a cycloalkyl group of 5 to 10 carbons, CH₂OCH₃ or CH₂OCH₂OOC₁₋₆alkyl, or R₈ is phenyl or C₁₋₆ alkylphenyl, R₉ and R₁₀ independently are hydrogen, an alkyl group of 1 to 10 carbons, or a cycloalkyl group of 5-10 carbons, or phenyl or C₁₋₆alkylphenyl, R₁₁ is alkyl of 1 to 6 carbons, phenyl or C₁₋₆alkylphenyl, R₁₂ is alkyl of 1 to 6 carbons, and R₁₃ is divalent alkyl radical of 2-5 carbons, or a pharmaceutically acceptable salt of said compound.

\* \* \* \* \*

UNITED STATES PATENT AND TRADEMARK OFFICE
CERTIFICATE OF CORRECTION

PATENT NO. : 7,476,673 B2
APPLICATION NO. : 11/015994
DATED : January 13, 2009
INVENTOR(S) : Tsang et al.

It is certified that error appears in the above-identified patent and that said Letters Patent is hereby corrected as shown below:

Col. 65, Line 65
In Claim 26, after the words "alkoxy of 1 to 10 carbons", insert --, or alkylthio of 1 to 10 carbons--;

Col. 67, Line 38
In Claim 28, after the word "tri-lower", delete "alkenyl" and insert therefor --alkylsilyl--;

Col. 69, Line 32
In Claim 31, delete "$R_3$ is H or alkylof 1 to 110 carbons" and insert therefor --$R_3$ is H or alkyl of 1 to 10 carbons--;

Col. 69, Line 47
In Claim 31, after the words "5 carbons," delete "or cycloalkyl of 3 to 5 carbons,";

Col. 70, Line 13
In Claim 33, after the words "alkyl of 1 to 6 carbons," delete "COOR3" and insert therefor --$COOR_3$--;

Col. 70, Line 30
In Claim 33, delete "$CR7(OR_{12})_2$" and insert therefor --$CR_7(OR_{12})_2$--;

Col. 71, Line 47
In Claim 35, after the words "alkyl of 1 to 6 carbons," delete "COOR3" and insert therefor --$COOR_3$--;

UNITED STATES PATENT AND TRADEMARK OFFICE
CERTIFICATE OF CORRECTION

PATENT NO.       : 7,476,673 B2
APPLICATION NO.  : 11/015994
DATED            : January 13, 2009
INVENTOR(S)      : Tsang et al.

It is certified that error appears in the above-identified patent and that said Letters Patent is hereby corrected as shown below:

Col. 73, Line 43
In Claim 37, after the words "1 to 6 carbons, and" delete "R13" and insert therefor --$R_{13}$--.

Signed and Sealed this

Seventeenth Day of March, 2009

JOHN DOLL
*Acting Director of the United States Patent and Trademark Office*

Disclaimer

7,476,673—Kwok Yin Tsang, Irvine, CA (US); Santosh Sinha, Ladera Ranch, CA (US); Xiaoxia Liu, Lake Forest CA (US); Smita Bhat, Irvine, CA (US); Roshantha A. Chandraratna, Laguna Hills, CA (US). DISUBSTITUTED CHANLCONE OXIMES AS SELECTIVE AGONISTS OF RARY RETINOID RECEPTORS. Patent dated January 13, 2009. Disclaimer filed August 8, 2011, by the assignee, Allergan, Inc., Irvine, CA (US).

Hereby disclaims all of the claims 1-38 of said patent.

*(Official Gazette November 22, 2011)*